(12) United States Patent
Seth et al.

(10) Patent No.: US 7,519,452 B2
(45) Date of Patent: Apr. 14, 2009

(54) MOBILE BRAIN-BASED DEVICE FOR USE IN A REAL WORLD ENVIRONMENT

(75) Inventors: Anil K. Seth, San Diego, CA (US); Jeffrey L. McKinstry, San Diego, CA (US); Gerald M. Edelman, La Jolla, CA (US); Jeffrey L. Krichmar, Cardiff-by-the-Sea, CA (US)

(73) Assignee: Neurosciences Research Foundation, Inc., San Diego, CA (US)

( * ) Notice: Subject to any disclaimer, the term of this patent is extended or adjusted under 35 U.S.C. 154(b) by 140 days.

(21) Appl. No.: 11/105,019

(22) Filed: Apr. 13, 2005

(65) Prior Publication Data

US 2005/0261803 A1 Nov. 24, 2005

Related U.S. Application Data

(60) Provisional application No. 60/562,376, filed on Apr. 15, 2004.

(51) Int. Cl.
- *G06F 15/18* (2006.01)
- *G06N 3/00* (2006.01)
- *G06F 15/00* (2006.01)
- *G05B 19/04* (2006.01)

(52) U.S. Cl. .................. 700/249; 700/250; 700/259; 706/13; 706/44

(58) Field of Classification Search .............. 700/245, 700/259, 249, 250, 47, 48; 706/2, 15, 25, 706/27, 44, 12, 13; 716/15; 703/11, 23
See application file for complete search history.

(56) References Cited

U.S. PATENT DOCUMENTS 6,687,686 B1 * 2/2004 Nervegna et al. ............. 706/15

(Continued)

OTHER PUBLICATIONS

Krichmar, Jeffery and Snook, James; A Neural Approach to Adaptive Behavior and Multi-Sensor Action Selection in a Mobile Device; May 2002; IEEE International Conference on Robotics & Automation; pp. 3864-3869.*

(Continued)

*Primary Examiner*—Thomas G Black
*Assistant Examiner*—Christine M Behncke
(74) *Attorney, Agent, or Firm*—Fliesler Meyer LLP

(57) ABSTRACT

A mobile brain-based device BBD includes a mobile base equipped with sensors and effectors (Neurally Organized Mobile Adaptive Device or NOMAD), which is guided by a simulated nervous system that is an analogue of cortical and sub-cortical areas of the brain required for visual processing, decision-making, reward, and motor responses. These simulated cortical and sub-cortical areas are reentrantly connected and each area contains neuronal units representing both the mean activity level and the relative timing of the activity of groups of neurons. The brain-based device BBD learns to discriminate among multiple objects with shared visual features, and associated "target" objects with innately preferred auditory cues. Globally distributed neuronal circuits that correspond to distinct objects in the visual field of NOMAD 10 are activated. These circuits, which are constrained by a reentrant neuroanatomy and modulated by behavior and synaptic plasticity, result in successful discrimination of objects. The brain-based device BBD is moveable, in a rich real-world environment involving continual changes in the size and location of visual stimuli due to self-generated or autonomous, movement, and shows that reentrant connectivity and dynamic synchronization provide an effective mechanism for binding the features of visual objects so as to reorganize object features such as color, shape and motion while distinguishing distinct objects in the environment.

4 Claims, 16 Drawing Sheets

U.S. PATENT DOCUMENTS

| | | | |
|---|---|---|---|
| 7,024,276 B2 * | 4/2006 | Ito | 700/245 |
| 2004/0128004 A1 * | 7/2004 | Adams et al. | 700/48 |
| 2004/0138780 A1 * | 7/2004 | Lewis | 700/245 |

OTHER PUBLICATIONS

Sinha, Sitabhra and Basak, Jayanta; Response of an Excitatory-Inhibitory Neural Network to External Stimulation: An Application to Image Segmentation; Sep. 1999; IEEE Conference Publication Artificial Neural Networks; pp. 803-808.*

Körner, Edgar and Matsumoto, Gen; Cortical Architecture and Self-Referential Control for Brain-Like Computation; Oct. 2002; IEEE Engineering in Medicine and Biology; pp. 121-133.*

Abeles, M., Role of the cortical neuron: integrator or coincidence detector? Israel Journal of Medical Sciences, 1982, pp. 83-92, vol. 18.

Almássy N. et al., Behavioral constraints in the development of neuronal properties: a cortical model embedded in a real-world device, Cerebral Cortex, Jun. 1998, pp. 346-361, vol. 8.

Aston-Jones, G. et al., Norepinephrine-containing locus coeruleus neurons in behaving rats exhibit pronounced responses to non-noxious environmental stimuli, Journal of Neuroscience, Aug. 1981, pp. 887-900, vol. 1, No. 8.

Azouz, R. et al., Dynamic spike threshold reveals a mechanism for synaptic coincidence detection in cortical neurons in vivo, Proceedings of the National Academy of Sciences of the United States of America, Jul. 5, 2000, pp. 8110-8115, vol. 97, No. 14.

Bienenstock, E.L. et al., Theory for the development of neuron selectivity: orientation specificity and binocular interaction in visual cortex, Journal of Neuroscience, Jan. 1982, pp. 32-48, vol. 2, No. 1.

Brooks, R., Intelligence without representation, Artificial Intelligence, 1991, pp. 139-160, vol. 47.

Chelazzi, L., et al.., Responses of neurons in inferior temporal cortex during memory-guided visual search. Journal of Neurophysiology, Dec. 1998, pp. 2918-2940, vol. 80.

Constantinidis, C. et al., Correlated discharges among putative pyramidal neurons and interneurons in the primate prefrontal cortex, Journal of Neurophysiology, Dec. 2002, pp. 3487-3497. vol. 88.

Edelman, G.M., Neural Darwinism: the theory of neuronal group selection, 1987, pp. 39, 59, 127-133, 149, 169-171, 219, 227-229, 231 & 327, [all of which relate to the "cortex" and "cortical" functions]. Basic Books. New York.

Edelman, G.M., Neural Darwinism: selection and reentrant signaling in higher brain function, Neuron, 1993, pp. 115-125, vol. 10.

Edelman, G.M., et al., Synthetic neural modeling applied to a real-world artifact, Proceedings of the National Academy of Sciences of the United States of America, Aug. 1992, pp. 7267-7271, vol. 89.

Engel, A.K., et al., Dynamic predictions: oscillations and synchrony in top-down processing, Nature Reviews Neuroscience, Oct. 2001, pp. 704-716, vol. 2.

Fries, P., et al., Modulation of oscillatory neuronal synchronization by selective visual attention, Science, Feb. 23, 2001, pp. 1560-1563, vol. 291.

Friston, K.J., et al. Value-dependent selection in the brain: simulation in a synthetic neural model, Neuroscience, 1994, pp. 229 243, vol. 59, No. 2.

Georgopoulos, A.P., et al., Neuronal population coding of movement direction, Science, Sep. 26, 1986, pp. 1416-1419, vol. 233.

Gray, C.M., The temporal correlation hypothesis of visual feature integration: still alive and well, Neuron, Sep. 1999, pp. 31-47, vol. 24.

Gray, C.M., et al., Stimulus-specific neuronal oscillations in orientation columns of cat visual cortex, Proceedings of the National Academy of Sciences of the United States of America, Mar. 1989, pp. 1698-1702, vol. 86.

Grossberg, S., The link between brain learning, attention, and consciousness, Consciousness and Cognition, Mar. 1999, pp. 1-44, vol. 8.

Izhikevich, E.M., et al., Relating STDP to BCM, Neural Computation, 2003, pp. 1511-1523, vol. 15.

Knoblauch, A., et al., Scene segmentation by spike synchronization in reciprocally connected visual areas. I. Local effects of cortical feedback, Biological Cybernetics, 2002, pp. 151-167, vol. 87.

Knoblauch, A., et al., Scene segmentation by spike synchronization in reciprocally connected visual areas. II. Global assemblies and synchronization on larger space and time scales, Biological Cybernetics, 2002, pp. 168-184, vol. 87.

König, P., et al., Integrator or coincidence detector? The role of the cortical neuron revisited, Trends in Neuroscience, 1996, pp. 130-137, vol. 19, No. 4.

Körner et al.; Cortical Architecture and Self-Referential Control for Brain-like Computation. IEEE Engineering in Medicine and Biology. Sep./Oct. 2002, pp. 121-133.

Krichmar, J.L., et al., Machine psychology: autonomous behavior, perceptual categorization and conditioning in a brain-based device, Cerebral Cortex, Aug. 2002, pp. 818-830, vol. 12.

Krichmar, J.L., et al., Experience-dependent perceptual categorization in a behaving real-world device, From Animals to Animats 6: Proceedings of the Sixth International Conference on the Simulation of Adaptive Behavior, 2000, pp. 41-50, MIT Press/Bradford Books, Cambridge, MA.

Krichmar J., et al., A Neural Approach to Adaptive Behavior and Multi-Sensor Action Selection in a Mobile Device. Proc. of the IEEE International Conference on Robotics & Automation. May 2002. pp. 3864-3869. Washington. D.C.

Krichmar, J., et al., Brain-Based Devices: Intelligent Systems Based on Principles of the Nervous System. Proc. of the IEEE/RSJ International Conference on Intelligent Robots and Systems. Oct. 2003, pp. 940-945, Las Vegas, NV.

Lee, C., et al., Population coding of saccadic eye movements by neurons in the superior colliculus, Nature, Mar. 24, 1988, pp. 357-360, vol. 332.

Montague, P.R., et al., A framework for mesencephalic dopamine systems based on predictive Hebbian learning, Journal of Neuroscience, Mar. 1, 1996, pp. 1936-1947, vol. 16, No. 5.

Raizada, R.D., et al., Towards a theory of the laminar architecture of cerebral cortex: computational clues from the visual system, Cerebral Cortex, Jan. 2003, pp. 100-113, vol. 13.

Reeke, G.N., et al., Synthetic neural modeling: the 'Darwin' series of recognition automata, Proceedings of the IEEE, Sep. 1990, pp. 1498-1530, vol. 78, No. 9.

Reynolds, J.H., et al., Attention increases sensitivity of V4 neurons, Neuron, Jun. 2000, pp. 703-714, vol. 26.

Schultz, W., et al., A neural substrate of prediction and reward, Science, Mar. 14, 1997, pp. 1593-1599, vol. 275.

Senn, W., et al., An algorithm for modifying neurotransmitter release probability based on pre- and postsynaptic spike timing, Neural Computation, 2000, pp. 35-67.

Shadlen, M.N., et al., Synchrony unbound: a critical evaluation of the temporal binding hypothesis, Neuron, Sep. 1999, pp. 67-77, vol. 24.

Shafritz, K.M., et al., The role of the parietal cortex in feature binding, Proceedings of the National Academy of Sciences of the United State sof America, Aug. 6, 2002, pp. 10917-10922, vol. 99, No. 16.

Singer, W., Neuronal synchrony: a versatile code for the definition of relations? Neuron, Sep. 1999, pp. 49-65, vol. 24.

Sinha et al., Response of an Excitatory-Inhibitory Neural Network to External Stimulation: An Application to Image Segmentation. Artificial Neural Networks, Conference Publication No. 470. Sep. 7-10, 1999. pp. 803-808.

Song, S., et al., Cortical development and remapping through spike timing-dependent plasticity, Neuron, Oct. 25, 2001, pp. 339-350, vol. 32.

Sporns, O., et al., Modeling perceptual grouping and figure-ground segregation by means of active reentrant connections, Proceedings of the National Academy of Sciences of the United States of America, Jan. 1991, pp. 129-133, vol. 88.

Sporns, O., et al., Plasticity in value systems and its role in adaptive behavior, Adaptive Behavior, 2000, pp. 129-148, vol. 8.

Srinivasan, R., et al., Increased synchronization of neuromagnetic responses during conscious perception, Journal of Neuroscience, Jul. 1, 1999, pp. 5435-5448, vol. 19, No. 13.

Steinmetz, P.N., et al., Attention modulates synchronized neuronal firing in primate somatosensory cortex, Nature, Mar. 9, 2000, pp. 187-190, vol. 404.

Thiele, A., et al., Neuronal synchrony does not correlate with motion coherence in cortical area MT, Nature, Jan. 23, 2003, pp. 366-370, vol. 421.

Tononi, G., et al., Reentry and the problem of integrating multiple cortical areas: simulation of dynamic integration in the visual system, Cerebral Cortex, Jul./Aug. 1992, pp. 310-335, vol. 2.

Treisman, A., The binding problem, Current Opinion in Neurobiology, 1996, pp. 171-178, vol. 6.

Treisman, A., Feature binding, attention and object perception, Phil. Trans. Royal Society London B Biol. Sci., 1998, pp. 1295-1306, vol. 353.

Ungerleider, L.G., et al., 'What' and 'where' in the human brain, Current Opinion in Neurobiology, 1994, pp. 157-165, vol. 4.

Von Der Malsburg, C., et al., Sensory segmentation with coupled neural oscillators, Biological Cybernetics, 1992, pp. 233-242, vol. 67.

Wray, J., et al., A model of color vision based on cortical reentry, Cerebral Cortex, Sep./Oct. 1996, pp. 701-716, vol. 6.

* cited by examiner

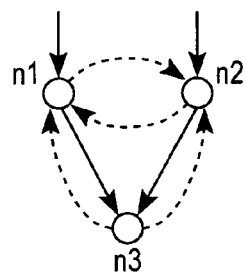
FIG. 3A
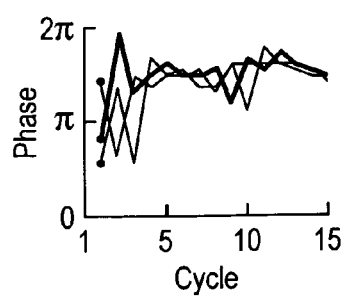
FIG. 3B
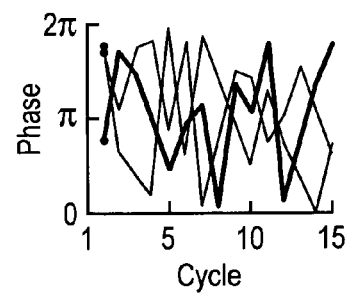
FIG. 3C
Reentry
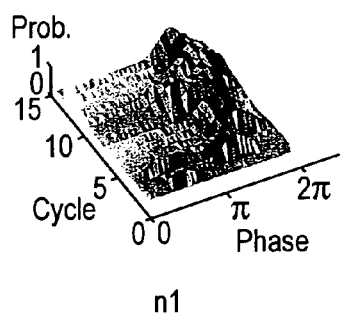
n1
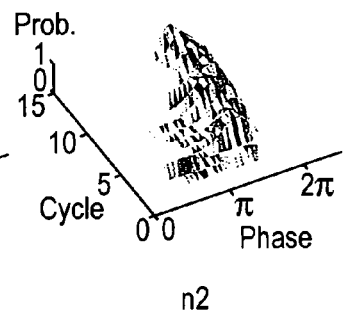
n2
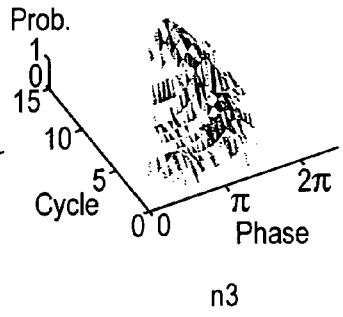
n3
FIG. 3D
No Reentry
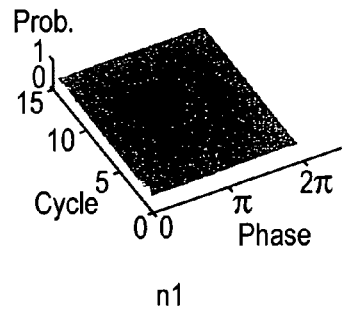
n1
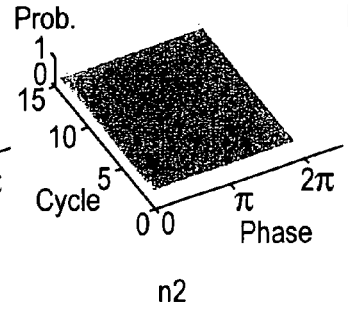
n2
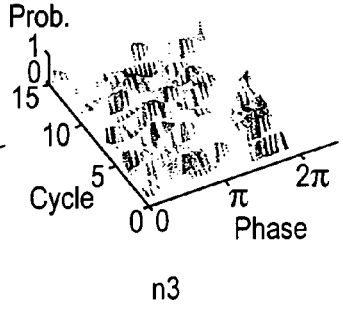
n3
FIG. 3E

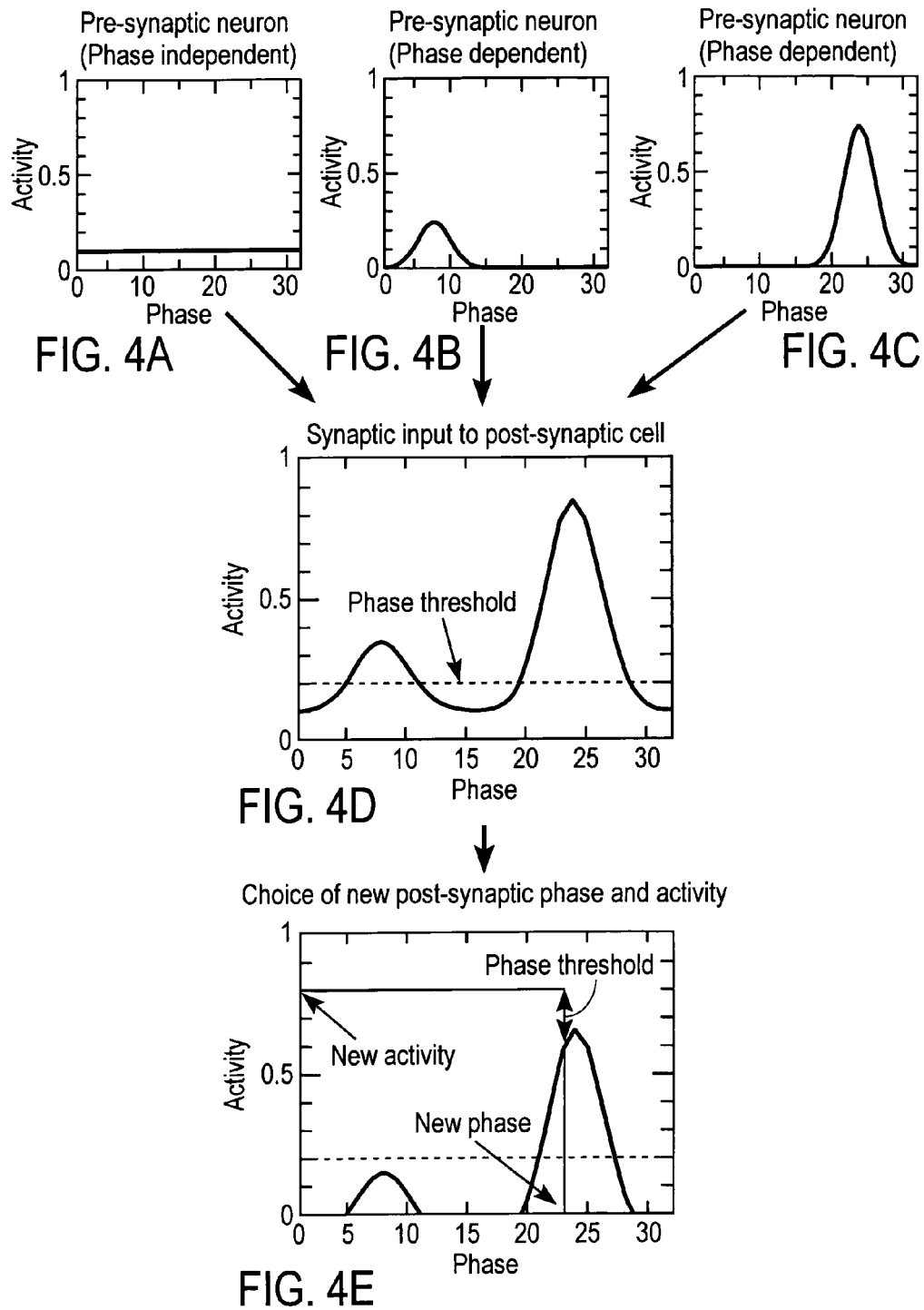

Training

Testing

MOBILE BRAIN-BASED DEVICE FOR USE IN A REAL WORLD ENVIRONMENT

PRIORITY CLAIM

This application claims priority under 35 U.S.C. 119(e) to U.S. Provisional Patent Application No. 60/562,376, filed Apr. 15, 2004, entitled "Mobile Brain-Based Device for Use in a Real World Environment," by Anil K. Seth et al., which application is incorporated herein by reference.

Statement Regarding Federally Sponsored Research And Development: This invention was made with Government support under N00014-03-1-0980 awarded by the Office of Naval Research. The United States Government has certain rights in the invention.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

The present invention relates to the field of brain-based devices having simulated nervous systems for guiding the behavior of the devices in a real world environment.

BACKGROUND OF THE INVENTION

A brain-based device is a device that has a sensing system for receiving information, effectors that enable the device to move about, and a simulated nervous system which controls movement of the effectors in response to input from the sensing system to guide the behavior of the brain-based device in a real-world environment. The sensing system may include video and audio sensors which receive image and audio information from the real-world environment in which the device moves. The simulated nervous system may be implemented as a computer-based system which receives and processes the image and auditory information input to the brain-based device and outputs commands to the effectors to control the behavior of the device in the environment.

The simulated nervous system, while implemented in a computer-based system, emulates the human brain rather than a programmed computer which typically follows a set of precise executable instructions or which performs computations. That is, the brain is not a computer and follows neurobiological rather than computational principles in its construction. The brain has special features or organization and functions that are not believed to be consistent with the idea that it follows such a set of precise instructions or that it computes in the manner of a programmed computer. A comparison of the signals that a brain receives with those of a computer shows a number of features that are special to the brain. For example, the real world is not presented to the brain like a data storage medium storing an unambiguous series of signals that are presented to a programmed computer. Nonetheless, the brain enables humans (and animals) to sense their environment, categorize patterns out of a multitude of variable signals, and initiate movement. The ability of the nervous system to carry out perceptual categorization of different signals for sight, sound, etc. and divide them into coherent classes without a prearranged code is special and unmatched by present day computers, whether based on artificial intelligence (AI) principles or neural network constructions.

The visual system of the brain contains a variety of cortical regions which are specialized to different visual features. For example, one region responds to the color of an object, another separate region responds to the object's shape, while yet another region responds to any motion of the object. The brain will enable a human to see and distinguish in a scene, for example, a red airplane from a gray cloud both moving across a background of blue sky. Yet, no single region of the brain has superordinate control over the separate regions responding to color, shape and movement that coordinate color, shape and movement so that we see and distinguish a single object (e.g. the airplane) and distinguish it from other objects in the scene (e.g. the cloud and the sky).

The fact that there is no such single superordinate control region in the brain poses what is known as the "binding problem." How do these functionally separated regions of the brain coordinate their activities in order to associate features belonging to individual objects and distinguish among different objects? It is this ability of the brain to so associate and distinguish different objects that enables us to move about in our real-world environment. A mobile brain-based device having a simulated nervous system that can control the behavior of the device in the rich environment of the real world therefore would have many advantages and uses.

Mechanisms proposed for solving the "binding problem" generally fall into one of two classes: (i) binding through the influence of "higher" attentional mechanisms of the brain, and (ii) selective synchronization of the "firing" of dynamically formed groups of neurons in the brain. In (i), the belief is that the brain through its parietal or frontal regions, "binds" objects by means of an executive mechanism, for example, a spotlight of attention that would combine visual features appearing at a single location in space, e.g. the red airplane or gray cloud against the background of a blue sky. In (ii), the belief is that the brain "binds" objects in an automatic, dynamic, and pre-attentive process through groups of neurons that become linked by selective synchronization of the firing of the neurons. These synchronized neuronal groups form within the brain into global patterns of activity, or circuits, corresponding to perceptual categories. This enables us to see, for example, a red, flying airplane as a single object distinct from other objects such as a gray, moving cloud.

Computer-based computational models of visual binding, as well as physical, mobile brain-based devices having a simulated nervous system, are known, Yet, neither provides emergent circuits in the computer model or in the simulated nervous system of the physical brain-based device that contribute to providing a device with a rich and variable behavior in the real-world environment, especially in environments that require preferential behavior towards one object among many in a scene. For example, it would be desirable to have a mobile brain-based device move about in an environment and have preferential behavior toward one object among many in a scene so as to be able to obtain images of that object via an on-board camera and to select that object via on-board grippers.

One prior computational computer model simulated the nervous system by representing nine neural areas analogous to nine cortical areas of the visual system of the brain. It also simulated "reward" and motor systems of the nervous system. The model had "reentrant connections" or circuits between the nine different cortical areas, which are connections that allow the cortical areas to interact with each other. This computational model showed the capabilities of reentrant circuits to result in binding; the computer model, however, had several limitations. The stimuli into the modeled nervous system came from a limited predefined set of simulated object shapes and these were of uniform scale, contrary to what is found in a real-world environment. Furthermore, the resulting modeled behavior did not emerge in a rich and noisy environment experienced by behaving organisms in the real world. A more detailed description of this computational model is given in the paper entitled "Reentry and the Problem of Integrating Multiple Cortical Areas: Simulation of Dynamic Integration in the Visual System", by Tononi and Edelman, *Cerebral Cortex*, July/August 1992.

A prior physical, mobile brain-based device having a simulated nervous system does explore its environment and through this experience learns to develop adaptive behaviors. Such a prior mobile brain-based device is guided by the simulated nervous system which is implemented on a computer system. The simulation of the nervous system was based on the anatomy and physiology of vertebrate nervous systems, but as with any simulated nervous system, with many fewer neurons and a simpler architecture than is found in the brain. For this physical, mobile brain-based device, the nervous system was made up of six major neural areas analogous to the cortical and subcortical brain regions. These six major areas included: an auditory system, a visual system, a taste system, a motor system capable of triggering behavior, a visual tracking system, and a value system. A detailed description of this mobile brain-based device is given in the paper entitled "Machine Psychology: Autonomous Behavior, Perceptual Categorization and Conditioning in a Brain-based Device" by Krichmar and Edelman, *Cerebral Cortex*, August 2002. While this brain-based device does operate in a real-world environment, it does not implement, among many other things, reentrant connections, thereby limiting its ability to engage in visually guided behavior and in object discrimination in a real-world environment.

SUMMARY OF THE INVENTION

The present invention is a physical, mobile brain-based device ("BBD") having a simulated nervous system for guiding the device in a rich exploratory and selective behavior in a real-world environment. The simulated nervous system of this device contains simulated neural areas analogous to the ventral stream of a brain's visual system, known as neural areas V1 V2, V4 and IT that influence visual tracking (neural area C), and neural areas having a value system (area S). These neural areas have reentrant connections within and between each other, which give rise to biases in motor activity, which in turn evoke behavioral responses in the mobile device enabling visual object discrimination in a scene.

Each neural area is comprised of many neuronal units. And, to represent the relative timing of neuronal activity, each neuronal unit in each neural area is described by a firing rate variable and a phase variable, where similar phases reflect synchronous firing. The binding problem, therefore, in the present invention is resolved based on principles of reentrant connectivity and synchronous neuronal firing.

The physical, mobile device of the present invention, as it is moving and interacting in the real world in a conditioning or training stage, learns what objects are in its environment, i.e. objects are not given to it as predefined data in a simulation. That is, the brain-based device of the present invention learns, in a given environment, what is a particular object, such as a green diamond, what is a floor, what is a wall, etc. Moreover, this learning through movement and interaction in the environment results in the brain-based device having invariant object recognition. This means that once it learns what, for example, a green diamond is as an object during a training stage, it will recognize that object when in a testing stage as the device moves about its real-world environment whether the object is across a room from the device, directly in front of the device, off to the left of the device, off to the right of the device, etc.

BRIEF DESCRIPTION OF THE DRAWINGS

FIGS. 3A-3E are views of a simple network of three neuronal units used to explain the neuroanatomy of the present invention shown in FIG. 2.

FIGS. 4A-4E illustrate graphically activity vs. phase of a neuronal unit.

DETAILED DESCRIPTION

Aspects of the invention are illustrated by way of example and not by way of limitation in the figures of the accompanying drawings in which like references indicate similar elements. It should be noted that references to "an", "one" and "various" embodiments in this disclosure are not necessarily to the same embodiment, and such references mean at least one. In the following description, numerous specific details are set forth to provide a thorough description of the invention. However, it will be apparent to one skilled in the art that the invention may be practiced without these specific details.

In other instances, well-known features have not been described in detail so as not to obscure the invention.

Figure 1:
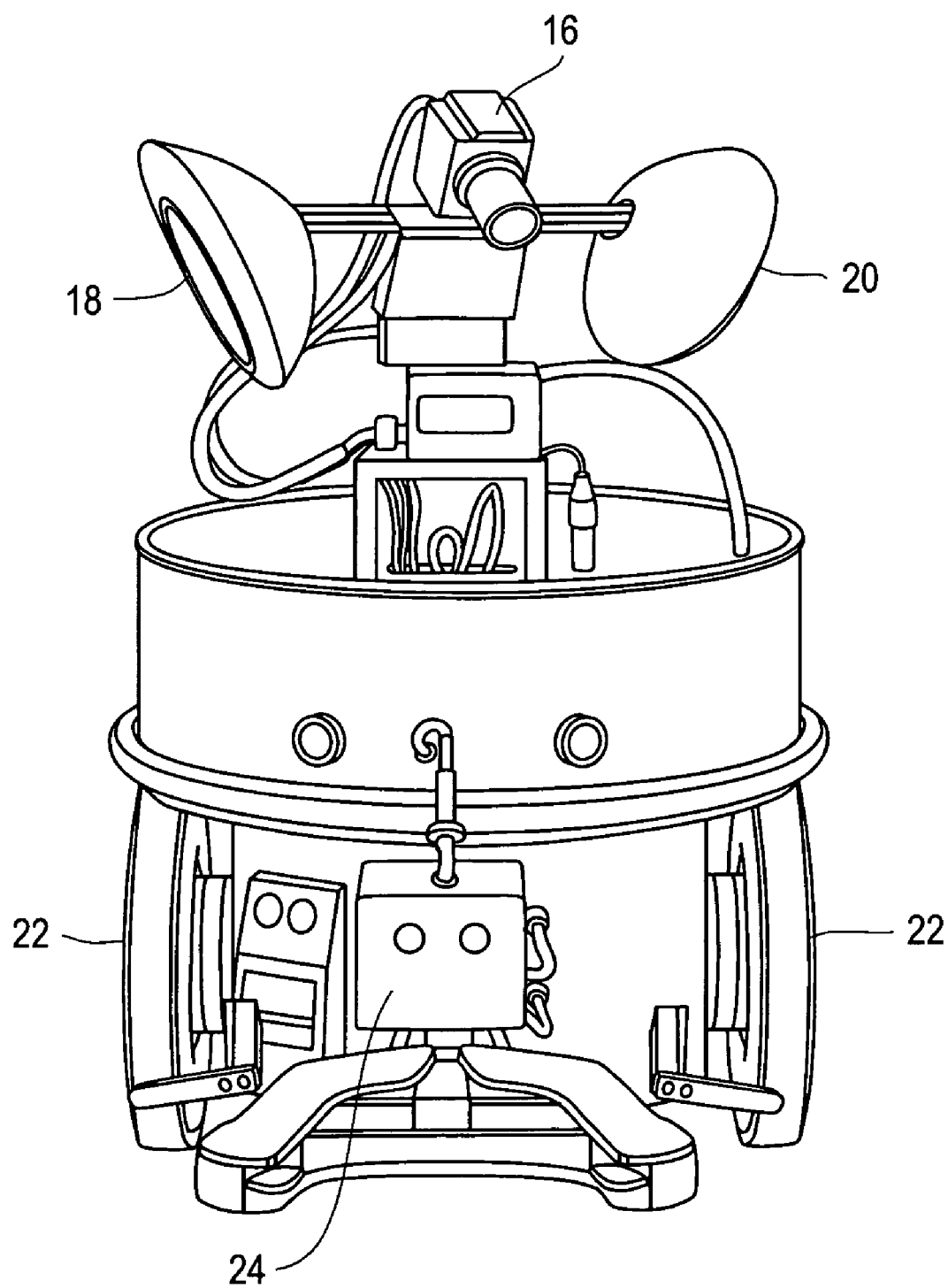
FIG. 1 is a pictorial view of a physical, mobile brain-based device.

FIG. 1 is a pictorial view of a brain-based device (BBD) of the present invention which includes physically instantiated mobile Neurally Organized Mobile Adaptive Device (NOMAD) 10 which can explore its environment and develop adaptive behavior while experiencing it. The brain-based device BBD also includes a simulated nervous system 12 (FIG. 2) for guiding NOMAD 10 in its real-world environment. In one embodiment, the simulated nervous system 12, as will be further described, can run on a cluster of computer workstations (see FIG. 13) remote from NOMAD 10. In this embodiment, NOMAD 10 and the computer workstations communicate with one another via wireless communication, thereby enabling untethered exploration of NOMAD 10.

NOMAD 10 develops or adapts its behavior by learning about the environment using the simulated nervous system 12. As NOMAD 10 moves autonomously in its environment, it will approach and view multiple objects that share visual features, e.g. same color, and have distinct visual features such as shape, e.g. red square vs. red triangle. NOMAD 10 can become conditioned through the learning experience to prefer one target object, e.g. the red diamond, over multiple distracters or non-target objects such as the red square and a green diamond of a scene in its vision. NOMAD 10 learns this preference behaviorally while moving in its environment by orienting itself towards the target object in response to an audible tone.

NOMAD 10 has a CCD camera 16 for vision and microphones 18, 20 on either side of camera 16, which can provide visual and auditory sensory input to simulated nervous system 12, as well as effectors or wheels 22 for movement. It also has an infrared (IR) sensor 24 at the front of NOMAD 10 for obstacle avoidance by sensing differences in reflectivity of the surface on which it moves, and for triggering reflexive turns of NOMAD 10 in its environment. NOMAD 10 also contains a radio modem to transmit status, IR sensor information, and auditory information to the computer workstation carrying out the neural simulation via simulated nervous system 12 and to receive motor commands from the simulated nervous system 12 to control effectors 22. Video output from camera 16 can be sent to the computer workstations via RF transmission. All behavioral activity of NOMAD 10, other than the IR reflexive turns, is evoked by signals received from simulated nervous system 12.

Figure 2:
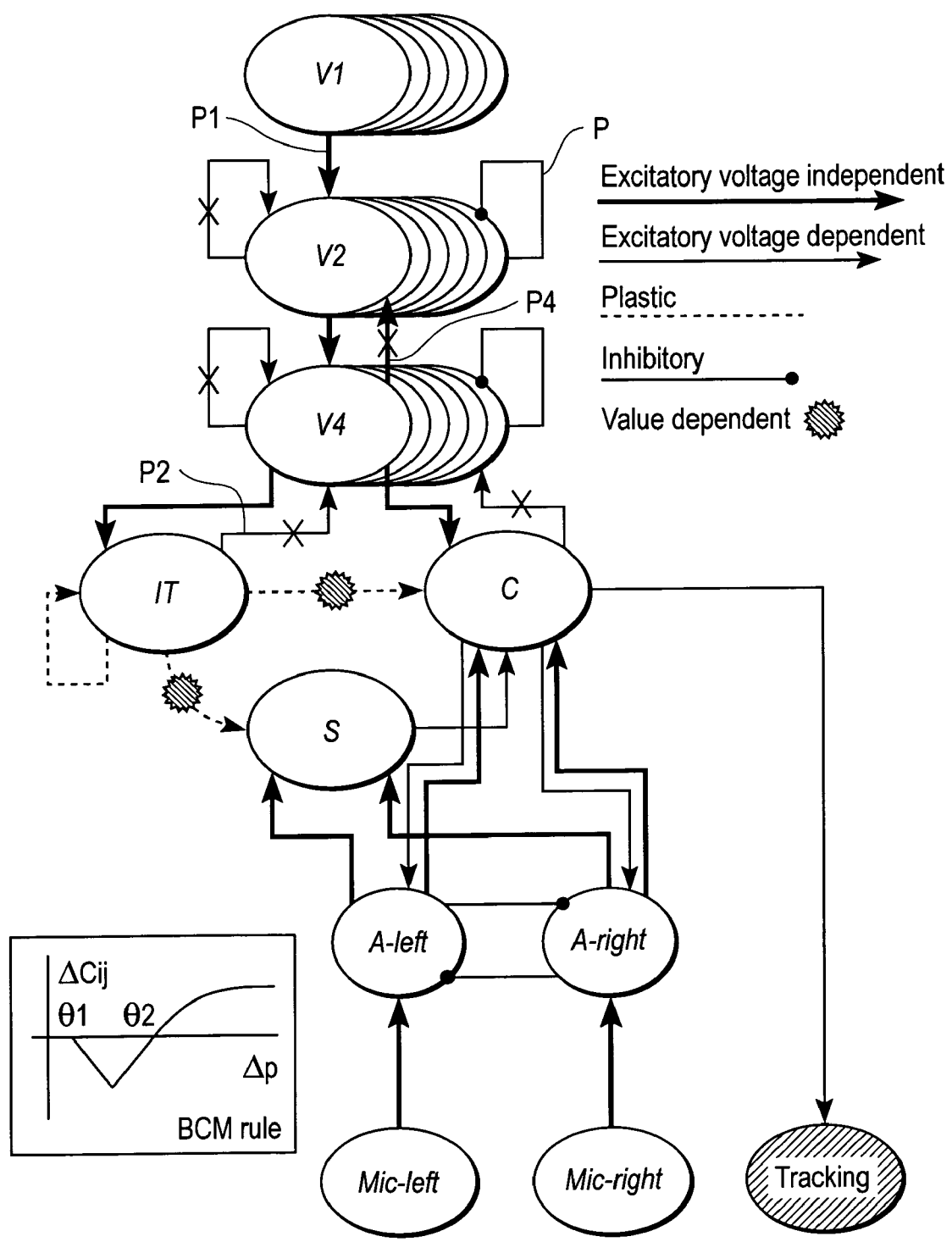
FIG. 2 is a schematic of the regional and functional neuroanatomy of the simulated nervous system of the brain-based device of FIG. 1.

FIG. 2 is a schematic diagram of the regional and functional neuroanatomy of simulated nervous system 12 which guides the behavior of NOMAD 10 in its environment. Simulated nervous system 12 is modeled on the anatomy and physiology of the mammalian nervous system but, as can be appreciated, with far fewer neurons and a much less complex architecture. Simulated nervous system 12 includes a number of neural areas labeled according to the analogous cortical and subcortical regions of the human brain. Thus, FIG. 2 shows respective neural areas labeled as V1, V2, V4, IT, S, A-left, Mic-left, A-right, Mic-right and C, whose activity controls the tracking of NOMAD 10. Each neural area V1, V2, etc. contains different types of neuronal units, each of which represents a local population of neurons. Each ellipse shown in FIG. 2 (except "Tracking") denotes a different neural area, with each such area having many neuronal units. To distinguish modeled or simulated neural areas from corresponding regions in the mammalian nervous system, the simulated areas are indicated in italics, e.g. IT.

The neuroanatomy of FIG. 2 also shows schematically various projections P throughout the simulated nervous system 12. A projection can be "feedforward" from one neural area to another, such as the projection P1 from neural area V1 to neural area V2. A projection P may also be "reentrant" between neural areas such as the reentrant projection P2 from neural area IT to neural area V4 and reentrant projection P4 from neural area V4 to neural area V2. Reentrant projections P marked with an "X" were removed from the simulated nervous system 12 during "lesion" experiments as will be further described. Furthermore, projections P have properties as indicated by the legend in FIG. 2, which are (1) "excitatory voltage independent", (2) "excitatory voltage dependent", (3) "plastic", (4) "inhibitory," and (5) "value dependent."

The simulated nervous system 12 shown in FIG. 2 is comprised of four systems: a visual system, a tracking system, an auditory system and a value system.

FIG. 2—Visual System, Neural Areas V1, V2, V4, IT

The visual system is modeled on the primate occipitotemporal or ventral cortical pathway and includes neural areas V1→V2→V4→IT in which neurons in successive areas have progressively larger receptive fields until, in inferotemporal cortex, receptive fields cover nearly the entire visual field. Visual images from the CCD camera 16 of NOMAD 10 are filtered for color and edges and the filtered output directly influences neural activity in area V1. V1 is divided into subregions (not shown) each having neuronal units that respond preferentially to green (V1-green), red (V1-red), horizontal line segments (V1-horizontal), vertical line segments (V1-vertical), 45-degree lines (V1-diagonal-right), and 135-degree lines (V1-diagonal-left). This visual system provides a computationally tractable foundation for analyzing higher-level interactions within the visual system and between the visual system and other cortical areas.

Subregions of neural area V1 project topographically to corresponding subregions of neural area V2. The receptive fields of neuronal units in area V2 are narrow and correspond closely to pixels from the image of CCD camera 16. Neural area V2 has both excitatory and inhibitory reentrant connections within and among its subregions. Each V2 subregion projects to a corresponding V4 subregion topographically but broadly, so that neural area V4's receptive fields are larger than those of neural area V2. Neural area V4 subregions project back to the corresponding neural area V2 subregions with non-topographic reentrant connections. The reentrant connectivity within and among subregions of area V4 is similar to that in area V2. V4 projects in turn non-topographically to neural area IT so that each neuronal unit in neural area IT receives input from three V4 neuronal units randomly chosen from three different V4 subregions. Thus, while neuronal units in IT respond to a combination of visual inputs, the level of synaptic input into a given IT neuronal unit is fairly uniform; this prevents the activity of individual IT neuronal units from dominating the overall activity patterns. IT neuronal units project to other IT neuronal units through plastic connections, and back to neural area V4 through non-topographic reentrant connections.

FIG. 2—Tracking System—Neural Area C

The tracking system allows NOMAD 10 to orient towards auditory and visual stimuli. The activity of neural area C (analogous to the superior colliculus) dictates where NOMAD 10 directs its camera gaze. Tracking in NOMAD 10 is achieved by signals to wheels 22 based on the vector summation of the activity of the neuronal units in area C. Each neuronal unit in area C has a receptive field which matches its preferred direction, and the area has a topographic arrangement such that if activity is predominately on the left side of area C, signals to NOMAD 10's wheels 22 are issued that evoke a turn towards the left. The auditory neural areas (A-left and A-right) have strong excitatory projections to the respective ipsilateral sides of area C causing NOMAD 10 to orient towards a sound source. Neural area V4 projects topographically to area C, its activity causing NOMAD 10 to center its gaze on a visual object (e.g. a red triangle). Both neural areas IT and the value system S project to area C, and plastic connections in the pathways IT→C and IT→S facilitate target selection by creating a bias in activity, reflecting salient perceptual categories (see Value System, below). As will be described below, prior to a conditioning or training stage, because of a lack of bias, NOMAD 10 will direct its gaze predominately between two objects in its environment (e.g. a red triangle and a red square). After learning to prefer a visual object (e.g. a red triangle), changes in the strengths of the plastic connections result in greater activity in those parts of area C corresponding to the preferred object's position.

FIG. 2—Auditory System—Neural areas Mic-left, Mic-right, A-left, A-right

This system converts inputs from microphones 16, 18 into simulated neuronal unit activity. Neural areas Mic-left and Mic-right are respectively activated whenever the corresponding microphones 16, 18 detect a sound of sufficient amplitude within a specified frequency range. Mic-left/Mic-right project to neuronal units in areas A-left/A-right. Sound from one side results in activity on the ipsilateral side of the auditory system, which in turn produces activity on the ipsilateral side of area C causing orientation of NOMAD 10 towards the sound source.

FIG. 2—Value System—Neural Area S

Activity in the simulated value system signals the occurrence of salient sensory events and this activity contributes to the modulation of connection strengths in pathways IT→S and IT→C. Initially, in the learning stage to be described below, neural area S is activated by sounds detected by auditory system (see A-left→S and A-right→S of nervous system 12). Activity in area S is analogous to that of ascending neuromodulatory systems in that it is triggered by salient events, influences large regions of the simulated nervous system (described below in the section Synaptic Plasticity), and persists for several cycles. In addition, due to its projection to the tracking area C, area S has a direct influence on the behavior of NOMAD 10 in its real-world environment.

Details of the values of certain parameters of the neuronal units within the respective neural areas V1, V2, etc. shown in FIG. 2 are given in Table 1, described below. Details of the anatomical projections and connection types of neuronal units of the neural areas V1, V2, etc. are given in Table 2, described below. As is known, a neuronal unit can be considered pre- or post- a synapse (see "A Universe of Consciousness", by Edelman and Tononi, Basic Books, 2000, Fig. 4.3, for a description of a synapse and pre- and post-synaptic neurons.) The simulated nervous system 12 used in the experiments described below contains 28 neural areas V1, V2, etc., 53,450 neuronal units, and approximately 1.7 million synaptic connections.

Neuronal Units—Generally

In one embodiment, a neuronal unit within a neural area V1, V2, etc. of the simulated nervous system 12 is simulated by a mean firing rate model. The state of each neuronal unit is determined by both a mean firing rate variable ($\sigma$) and a phase variable (P). The mean firing rate variable of each neuronal unit corresponds to the average activity or firing rate of a group of roughly 100 neurons during a time period of approximately 100 milliseconds. The phase variable, which specifies the relative timing of firing activity, provides temporal specificity without incurring the computational costs associated with modeling of the spiking activity of individual neurons in real-time (see Neuronal Unit Activity and Phase, below).

Synaptic Connections—Generally

In one embodiment, synaptic connections between neuronal units, both within a given neural area, e.g. V1 or C, and between neural areas, e.g. V2→V4 or C→V4, are set to be either voltage-independent or voltage-dependent, either phase-independent or phase-dependent, and either plastic or non-plastic, as indicated by the legend in FIG. 2. Voltage-independent connections provide synaptic input to a post-synaptic neuron regardless of the post-synaptic state of the neuron. Voltage-dependent connections represent the contribution of receptor types (e.g. NMDA receptors) that require post-synaptic depolarization to be activated. In other words, a pre-synaptic neuron will send a signal along its axon through a synapse to a post-synaptic neuron. The post-synaptic neuron receives this signal and integrates it with other signals being received from other pre-synaptic neurons.

A voltage independent connection is such that if a pre-synaptic neuron is firing at a high rate, then a post-synaptic neuron connected to it via the synapse will fire at a high rate.

A voltage dependent connection is different. If the post-synaptic neuron is already firing at some rate when it receives a pre-synaptic input signal, then the voltage-dependent connection will cause the post-synaptic neuron to fire more. Since the post-synaptic neuron is active, i.e. already firing, this neuron is at some threshold level. Therefore, the pre-synaptic connection will modulate the post-synaptic neuron to fire even more. The voltage-dependent connection, no matter how active the pre-synaptic neuron is, would have no affect on the post-synaptic neuron if the latter were not above the threshold value. That is, the post-synaptic neuron has to have some given threshold of activity to be responsive or modulated by a voltage-dependent synaptic connection.

In the simulated nervous system 12 of FIG. 2, all within-neural area excitatory connections and all between-neural area reentrant excitatory connections are voltage-dependent (see FIG. 2 and Table 2). These voltage-dependent connections, as described above, play a modulatory role in neuronal dynamics.

Phase-dependent synaptic connections influence both the activity, i.e. firing rate, and the phase of post-synaptic neuronal units, whereas phase-independent synaptic connections influence only their activity. All synaptic pathways in the simulated nervous system 12 are phase-dependent except those involved in motor output (see Table 2: A-left/A-right→C, C⇆C) or sensory input (see Table 2: Mic-left/Mic-right→A-left/A-right, A-left⇆A-right, V1→V2), since signals at these interfaces are defined by magnitude only. Plastic connections are either value-independent or value-dependent, as described below.

Neuronal Synchrony in a Simple Network Model

FIGS. 3A-3E illustrate how reentrant connections among neuronal units can lead to neuronal synchrony in a mean firing rate model with a phase parameter as indicated above and, thereby, help solve the "binding problem" described above. FIG. 3A illustrates a simple network model consisting of three neuronal units (n1-n3). Units n1 and n2 receive, respectively, steady phase-independent input (solid input arrows) and project via respective voltage-independent connections to the third neuronal unit n3 (solid input arrows). Units n1 and n2 project to each other and unit n3 projects back to both units n1 and n2, via reentrant voltage-dependent connections (shown by dotted arrows).

FIG. 3B is a graph of phase vs. cycle and shows that in this simplified model all neuronal units n1-n3 become synchronized within 10 simulation cycles. By contrast, if reentrant connections are removed (the dotted arrows in FIG. 3A being "lesioned") so that only feedforward projections remain (the remaining solid arrows in FIG. 3A), synchrony is not achieved, as shown by the graph of FIG. 3C. While for clarity FIGS. 3B-3C show only the first 15 simulation cycles, these cycles are representative of network behavior in the real world of NOMAD 10 over long durations such as 10,000 cycles.

FIGS. 3D and 3E show the probability distributions from which postsynaptic phases are chosen for each neuronal unit. With reentrant connections intact (FIG. 3D), distributions for all neurons n1-n3 become peaked at the same phase. With reentrant connections absent, i.e. no reentry ("lesioned" networks, FIG. 3E), the probability distributions for neuronal units n1 and n2 remain flat due to their phase-independent inputs, and the distribution for unit n3 varies randomly over time.

To explore whether the synaptic property of connection strength is important for network behavior, the above analysis was repeated several times using different random seeds, and a network was compared in which all weights were set to a mean value (1.45). After 10,000 cycles, qualitatively identical results occurred to those shown in FIGS. 3B-3E. To explore the effect of the property of connection plasticity, the above was repeated for networks in which value-independent plasticity was enabled for the feedforward projections for neuronal units n1→n3 and n2→n3 (solid arrows). As before, networks were analyzed with randomly selected weights as well as networks with all weights set to a mean value (1.45). In both of these cases, synchrony in intact reentry networks and no synchrony in lesioned networks occurred. Also, since pre- and post-synaptic neuronal units were correlated in activity and phase, plastic connections in the intact networks increased in strength by nearly 100% over 1000 cycles. In lesioned networks, however, because pre- and post-synaptic units were not in phase with each other and these connections were depressed to about 10% of their initial values over the same duration.

The above indicate the importance of reentry connections to the "binding problem." That is, the results from this reduced model of FIG. 3A show that the presence of reentrant connections can facilitate synchronous activity among neural areas, that this synchrony does not depend on specific or differential connection strengths, and that the absence of reentry is not compensated by synaptic plasticity. The simulated nervous system 12 of the present invention has three major differences from this reduced model of FIG. 3A. System 12 has a large-scale reentrant neuroanatomy based on the vertebrate visual cortex as shown schematically in FIG. 2 and detailed in Table 1 and Table 2 below; it involves value-dependent and value-independent synaptic plasticity; and it allows NOMAD 10 to behave autonomously in a real-world environment.

Neuronal Unit Activity and Phase—Details

In various embodiments, the mean firing rate (s) of each neuronal unit ranges continuously from 0 (quiescent) to 1 (maximal firing). The phase (p) is divided into 32 discrete bins representing the relative timing of activity of the neuronal units by an angle ranging from 0 to $2\pi$. The state of a neuronal unit is updated as a function of its current state and contributions from voltage-independent, voltage-dependent, and phase-independent synaptic connectors. The voltage-independent input c to neuronal unit i from a unit j is:

$$A_{ij}^{VI}(t) = c_{ij}s_j(t),$$

where $s_j(t)$ is the activity of unit j, and $c_{ij}$ is the connection strength from unit j to unit i. The voltage-independent post-synaptic influence on unit i is calculated by convolving this value into a cosine-tuning curve over all phases:

$$POST_i^{VI} = \sum_{l=1}^{M} \sum_{j=1}^{N_l} \left( A_{ij}^{VI}(t) \sum_{k=1}^{32} \left( \frac{\cos((2\pi/32)(k - p_j(t))) + 1}{2} \right)^{tw} \right),$$

where M is the number of different anatomically defined connection types (see Table 2); $N_i$ is the number of connections of type M projecting to neuronal unit i; $p_j(t)$ is the phase of neuronal unit j at time t; and tw is the tuning width, which, in one embodiment, may be set to 10 so that the width of the tuning curve is relatively sharp (~5 phase bins).

The voltage-dependent input to neuronal unit i from unit j is:

$$A_{ij}^{VD}(t) = \Phi(POST_i^{VI}(p_j(t)))_{c_{ij}s_j}(t), \text{ where } \Phi(x) = \begin{cases} 0; & x < \sigma_i^{vdep} \\ x; & \text{otherwise} \end{cases},$$

where $\sigma_i^{vdep}$ is a threshold for the post-synaptic activity below which voltage-dependent connections have no effect (see Table 1).

The voltage-dependent post-synaptic influence on unit i is given by:

$$POST_i^{VD} = \sum_{l=1}^{M} \sum_{j=1}^{N_l} \left( A_{ij}^{VD}(t) \sum_{k=1}^{32} \left( \frac{\cos((2\pi/32)(k - p_j(t))) + 1}{2} \right)^{tw} \right).$$

The phase-independent activation into unit i from unit j is:

$$A_{ij}^{PI}(t) = c_{ij}s(t)$$

The phase-independent post-synaptic influence on unit i is a uniform distribution based on all the phase-independent inputs divided by the number of phase bins (32).

$$POST_i^{PI}(p) = \sum_{l=1}^{M} \sum_{j=1}^{N_l} \left( \frac{A_{ij}^{PI}(t)}{32} \right)$$

A new phase, $p_i(t+1)$, and activity, $s_i(t+1)$ are chosen based on a distribution created by linearly summing the post-synaptic influences on neuronal unit i (see FIGS. 4A-4E):

$$POST_i = \sum_{j=1}^{N_{VI}} POST_j^{VI} + \sum_{k=1}^{N_{VD}} POST_k^{VD} + \sum_{l=1}^{N_{PI}} POST_l^{PI}$$

The phase threshold, $\sigma_i^{phase}$, of the neuronal unit is subtracted from the distribution $POST_i$ and a new phase, $p_i(t+1)$, is calculated with a probability proportional to the resulting distribution (FIG. 4E). If the resulting distribution has an area less than zero (i.e. no inputs are above the phase threshold), a new phase, $p_i(t+1)$, is chosen at random. The new activity for the neuronal unit is the activity level at the newly chosen phase, which is then subjected to the following activation function:

$$s_i(t+1) = \phi(\tanh(g_i(POST_i(p_i(t+1)) + \omega s_i(t)))),$$

$$\text{where } \phi(x) = \begin{cases} 0; & x < \sigma_i^{fire} \\ x; & \text{otherwise} \end{cases},$$

where $\omega$ determines the persistence of unit activity from one cycle to the next, $g_i$ is a scaling factor, and $\sigma_i^{fire}$ a unit specific firing threshold.

Specific parameter values for neuronal units are given in Table 1, and synaptic connections are specified in Table 2.

TABLE 1

| | Neuronal unit parameters. | | | | | |
|---|---|---|---|---|---|---|
| Area | Size | σ-fire | σ-phase | σ-vdep | ω | g |
| V1 (6) | 60 × 80 | — | — | — | — | — |
| V2 (6) | 30 × 40 | 0.10 | 0.45 | 0.05 | 0.30 | 1.0* |
| V4 (6) | 15 × 20 | 0.20 | 0.45 | 0.10 | 0.50 | 1.0* |
| C | 15 × 20 | 0.10 | 0.10 | 0.10 | 0.50 | 1.0 |
| IT | 30 × 30 | 0.10 | 0.20 | 0.10 | 0.75 | 1.0 |
| S | 4 × 4 | 0.10 | 0.00 | 0.00 | 0.15 | 1.0 |
| Mic-right | 1 × 1 | — | — | — | — | — |
| Mic-left | 1 × 1 | — | — | — | — | — |

TABLE 1-continued

| | Neuronal unit parameters. | | | | | |
|---|---|---|---|---|---|---|
| Area | Size | σ-fire | σ-phase | σ-vdep | ω | g |
| A-left | 4 × 4 | 0.00 | 0.00 | 0.10 | 0.50 | 1.0 |
| A-right | 4 × 4 | 0.00 | 0.00 | 0.10 | 0.50 | 1.0 |

As shown in Table 1, area V1 is an input neural area and its activity is set based on the image of camera 16 of FIG. 1. Neural areas V1, V2 and V4 have six sub-areas each with neuronal units selective for color (e.g. red and green), and line orientation (e.g. 0, 45, 90 and 135 degrees). Neural areas Mic-left and Mic-right are input neural areas and their activity is set based on inputs from microphones 18, 20 (FIG. 1).

Table 1 also indicates the number of neuronal units in each neural area or sub-area ("Size" column). Neuronal units in each area apart from neural areas V1, Mic-left and Mic-right have a specific firing threshold (σ-fire), a phase threshold (σ-phase), a threshold above which voltage-dependent connections can have an effect (σ-vdep), a persistence parameter (ω), and a scaling factor (g). Asterisks in Table 1 mark values that are set to 1.0 for simulated nervous system 12 (FIG. 2) with lesioned reentrant connections (see Table 2).

TABLE 2

| Properties of anatomical projections and connection types. | | | | | | | | | |
|---|---|---|---|---|---|---|---|---|---|
| Projection | Arbor | P | $c_{ij}(0)$ | type | η | θ₁ | θ₂ | k1 | k2 |
| V1→V2 | □0 × 0 | 1.00 | 1, 2 | PI | 0.00 | 0 | 0 | 0.00 | 0.00 |
| V2→V2(intra) | □3 × 3 | 0.75 | 0.45, 0.85 | VD | 0.00 | 0 | 0 | 0.00 | 0.00 |
| V2→V2(inter) (X) | □2 × 2 | 0.40 | 0.5, 0.65 | VD | 0.00 | 0 | 0 | 0.00 | 0.00 |
| V2→V2(intra) | ⊖18, 25 | 0.10 | −0.05, −0.1 | VI | 0.00 | 0 | 0 | 0.00 | 0.00 |
| V2→V2(inter) | □2 × 2 | 0.05 | −0.05, −0.1 | VI | 0.00 | 0 | 0 | 0.00 | 0.00 |
| V2→V4 | □3 × 3 | 0.40 | 0.1, 0.12 | VI | 0.00 | 0 | 0 | 0.00 | 0.00 |
| V4→V2 (X) | □1 × 1 | 0.10 | 0.25, 0.5 | VD | 0.00 | 0 | 0 | 0.00 | 0.00 |
| V4→V4(inter) (X) | □2 × 2 | 0.40 | 1.75, 2.75 | VD | 0.00 | 0 | 0 | 0.00 | 0.00 |
| V4→V4(intra) | ⊖10, 15 | 0.10 | −0.15, −0.25 | VI | 0.00 | 0 | 0 | 0.00 | 0.00 |
| V4→V4(inter) | ⊖10, 15 | 0.10 | −0.15, −0.25 | VI | 0.00 | 0 | 0 | 0.00 | 0.00 |
| V4→V4(inter) | □2 × 2 | 0.03 | −0.15, −0.25 | VI | 0.00 | 0 | 0 | 0.00 | 0.00 |
| V4→C | □3 × 3 | 1.00 | 0.002, 0.0025 | VI | 0.00 | 0 | 0 | 0.00 | 0.00 |
| V4→IT | special | — | 0.1, 0.15 | VI | 0.00 | 0 | 0 | 0.00 | 0.00 |
| IT→V4 (X) | non-topo | 0.01 | 0.05, 0.07 | VD | 0.00 | 0 | 0 | 0.00 | 0.00 |
| IT→IT | non-topo | 0.10 | 0.14, 0.15 | VD | 0.10 | 0 | 0.866 | 0.90 | 0.45 |
| IT→C # | non-topo | 0.10 | 0.2, 0.2 | VD | 1.00 | 0 | 0.707 | 0.45 | 0.65 |
| IT→S # | non-topo | 1.00 | 0.0005, 0.001 | VI | 0.10 | 0 | 0.707 | 0.45 | 0.45 |
| C→V4 (X) | non-topo | 0.01 | 0.05, 0.07 | VD | 0.00 | 0 | 0 | 0.00 | 0.00 |
| C→C | ⊖6, 12 | 0.50 | −0.05, −0.15 | PI | 0.00 | 0 | 0 | 0.00 | 0.00 |
| C→Mleft | non-topo | 1.00 | 35, 35 | VD | 0.00 | 0 | 0 | 0.00 | 0.00 |
| C→Mright | non-topo | 1.00 | 35, 35 | VD | 0.00 | 0 | 0 | 0.00 | 0.00 |
| S→C | non-topo | 0.50 | 0.5, 05 | VD | 0.00 | 0 | 0 | 0.00 | 0.00 |
| S→S | non-topo | 0.50 | 0.7, 0.8 | VD | 0.00 | 0 | 0 | 0.00 | 0.00 |
| A-left→C | left-only | 1.00 | 0.5, 0.5 | VD | 0.00 | 0 | 0 | 0.00 | 0.00 |
| A-right→C | right-only | 1.00 | 0.5, 0.5 | VD | 0.00 | 0 | 0 | 0.00 | 0.00 |
| A-left→C | right-only | 1.00 | −0.15, −0.15 | PI | 0.00 | 0 | 0 | 0.00 | 0.00 |
| A-right→C | left-only | 1.00 | −0.15, −0.15 | PI | 0.00 | 0 | 0 | 0.00 | 0.00 |
| A-left→S | non-topo | 1.00 | 35, 35 | VD | 0.00 | 0 | 0 | 0.00 | 0.00 |
| A-right→S | non-topo | 1.00 | 35, 35 | VD | 0.00 | 0 | 0 | 0.00 | 0.00 |
| A-left ↔ A-right | non-topo | 1.00 | −1, −1 | PI | 0.00 | 0 | 0 | 0.00 | 0.00 |
| A-left ↔ A-right | non-topo | 1.00 | −0.5, −0.5 | VD | 0.00 | 0 | 0 | 0.00 | 0.00 |
| Mic-left, Mic-right→A-left, A-right | non-topo | 1.00 | 5, 5 | PI | 0.00 | 0 | 0 | 0.00 | 0.00 |

Table 2 shows properties of anatomical projections and connection types of simulated nervous system 12. A pre-synaptic neuronal unit connects to a post-synaptic neuronal unit with a given probability (P) and given projection shape (Arbor). This arborization shape can be rectangular "▢" with a height and width (h×w), doughnut shaped "Θ" with the shape constrained by an inner and outer radius (r1, r2), left-only (right-only) with the pre-synaptic neuronal unit only projecting to the left (right) side of the post-synaptic area, or non-topographical ("non-topo") where any pairs of pre-synaptic and post-synaptic neuronal units have a given probability of being connected. The initial connection strengths, $C_{ij}$(O), are set randomly within the range given by a minimum and maximum value (min, max). A negative value for $C_{ij}$(O), indicates inhibitory connections. Connections marked with "intra" denote those within a visual sub-area and connections marked with "inter" denote those between visual sub-areas. Inhibitory "inter" projections connect visual sub-areas responding to shape only or to color only (e.g. V4-red⇆V4-green, V4-horizontal⇆V4-vertical), excitatory "inter" projections connect shape sub-areas to color sub-areas (e.g. V4-red⇆V4-vertical). Projections marked # are value-dependent. A connection type can be phase-independent/voltage-independent (PI), phase-dependent/voltage-independent (VI), or phase-dependent/voltage-dependent (VD). Non-zero values for $\eta$, $\theta_1$, $\theta_2$, $k_1$, and $k_2$ signify plastic connections. The connection from V4 to IT was special in that a given neuronal unit in area IT was connected to three neuronal units randomly chosen from three different V4 sub-areas. Projections marked with an "X" were removed during lesion experiments.

In this model of a neuronal unit, post-synaptic phase tends to be correlated with the phase of the most strongly active pre-synaptic inputs. This neuronal unit model facilitates the emergence of synchronously active neuronal circuits in both a simple network (see FIG. 3A above, Neuronal Synchrony in a Simple Network Model) and in the full simulated nervous system (FIG. 2), where such emergence involves additional constraints imposed by reentrant connectivity, plasticity, and behavior.

Synaptic Plasticity.

Synaptic strengths are subject to modification according to a synaptic rule that depends on the phase and activities of the pre- and post-synaptic neuronal units. Plastic synaptic connections are either value-independent (see IT→IT in FIG. 2) or value-dependent (see IT→S, IT→C in FIG. 2). Both of these rules are based on a modified BCM learning rule in which thresholds defining the regions of depression and potentiation are a function of the phase difference between the pre-synaptic and post-synaptic neuronal units (see FIG. 2, inset). The graphical inset shown in FIG. 2 shows a form of the known BCM rule in which synaptic change ($\Delta C_{ij}$) is a function of the phase difference between post- and pre-synaptic neuronal units ($\Delta P$) and two thresholds ($\theta_1$ and $\theta_2$).

Synapses between neuronal units with strongly correlated firing phases are potentiated and synapses between neuronal units with weakly correlated phases are depressed; the magnitude of change is determined as well by pre- and post-synaptic activities. This learning rule is similar to a spike-time dependent plasticity rule applied to jittered spike trains where the region of potentiation has a high peak and a thin tail, and the region of depression has a comparatively small peak and fat tail.

Value-independent synaptic changes in $c_{ij}$ are given by:

$$\Delta_{c_{ij}}(t+1) = \eta s_i(t) s_j(t) BCM(\Delta p),$$

where $s_i(t)$ and $s_j(t)$ are activities of post- and pre-synaptic units, respectively, $\eta$ is a fixed learning rate, and $$\Delta p = \frac{\cos((2\pi/32)(p_i(t) - p_j(t))) + 1}{2},$$

where $p_i(t)$ and $p_j(t)$ are the phases of post- and pre-synaptic units ($0.0 \leq \Delta p \leq 1.0$). A value of $\Delta p$ near 1.0 indicates that pre- and post-synaptic units have similar phases, a value of $\Delta p$ near 0.0 indicates that pre- and post-synaptic units are out of phase. The function BCM is implemented as a piecewise linear function, taking $\Delta p$ as input, that is defined by two thresholds ($\theta_1$, $\theta_2$, in radians), two inclinations ($k_1$, $k_2$) and a saturation parameter $\rho$ ($\rho=6$ throughout):

$$BCM(\Delta p) = \begin{cases} 0; & \Delta p < \theta_1 \\ k_1(\theta_1 - \Delta p); & \theta_1 \leq \Delta p < (\theta_1 + \theta_2)/2 \\ k_1(\Delta p - \theta_2); & (\theta_1 + \theta_2)/2 \leq \Delta p < \theta_2 \\ k_2 \tanh(\rho(\Delta p - \theta_2))/\rho; & \text{otherwise} \end{cases}$$

Specific parameter settings for fine-scale synaptic confections are given in Table 2.

The rule for value-dependent synaptic plasticity differs from the value-independent rule in that an additional term, based on the activity and phase of the value system (neural areas), modulates the synaptic strength changes. Synaptic connections terminating on neuronal units that are in phase with the value system are potentiated, and connections terminating on units out of phase with the value system are depressed.

The synaptic change for value-dependent synaptic plasticity is given by:

$$\Delta_{c_{ij}}(t+1) = \eta s_i(t) s_j(t) BCM(\Delta p) V(t) BCM_v(\Delta p_v),$$

where $V(t)$ is the mean activity level in the value areas S at time t. Note that the $BCM_v$ function is slightly different than the BCM function above in that it uses the phase difference between area S and the post-synaptic neuronal unit as input $$(\Delta p_v = \frac{\cos((2\pi/32)(p_V(t) - p_i(t))) + 1}{2},$$

where $p_v(t)$ is the mean phase in area S. When both BCM and $BCM_v$ return a negative number, $BCM_v$ is set to 1 to ensure that the synaptic connection is not potentiated when both the pre-synaptic neuronal unit and value system (neural areas) are out of phase with the post-synaptic neuronal unit.

Simulated Cycle Computation.

During each simulation cycle of simulated nervous system 12, sensory input is processed, the states of all neuronal units are computed, the connection strengths of all plastic connections are determined, and motor output is generated. In experiments described below, execution of each simulated cycle required approximately 100 milliseconds of real time.

Experimental Conditions.

Figure 5A:
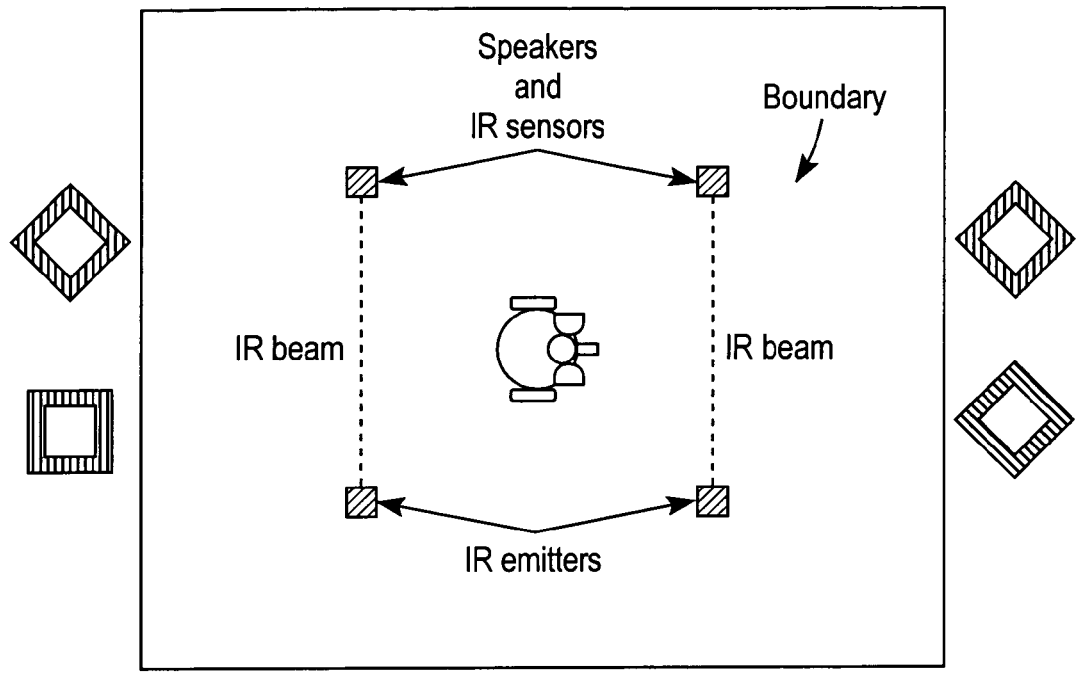
FIGS. 5A-5B illustrates schematically and photographically, respectively, an experimental set-up of a real-world environment in which the mobile brain-based device of FIGS. 1 and 2 behaves.
Figure 5B:
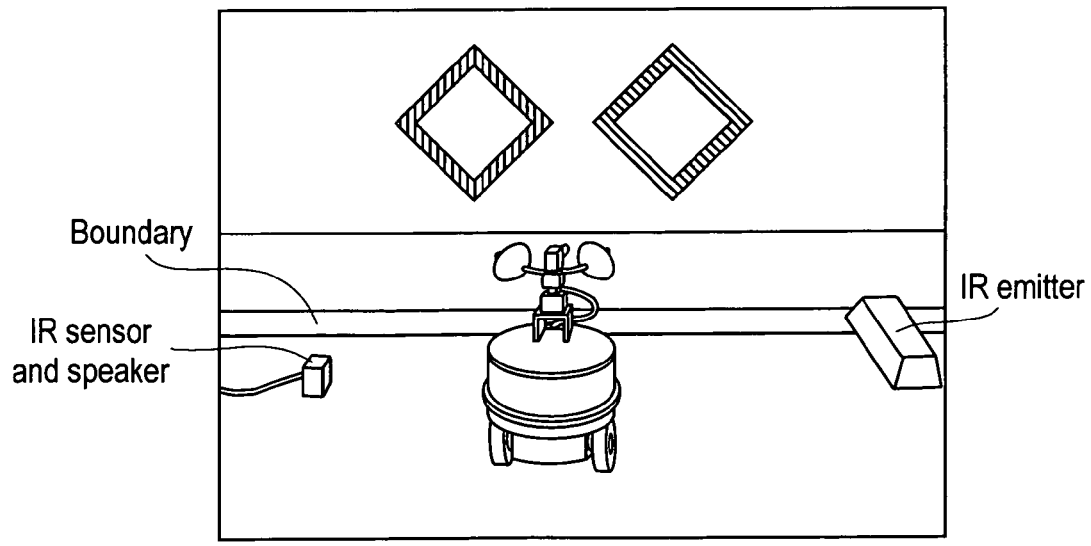

FIG. 5A shows a diagram of the environment of NOMAD 10. The environment consisted of an enclosed area with black walls. Various pairs of shapes from a set consisting of a green diamond, a green square, a red diamond, and a red square were hung on two opposite walls. The floor was covered with opaque black plastic panels, and contained a boundary made of reflective construction paper. When this boundary was detected by the infrared (IR) detector attached to the front of NOMAD 12 and facing toward the floor, NOMAD 10 made one of two reflexive movements: (i) if an object was in its visual field, it backed up, stopped and then turned roughly 180 degrees, (ii) if there was no object in its visual field, NOMAD 10 turned roughly 90 degrees, thus orienting away from walls without visual stimuli. Near the boundary of walls containing visual shapes, infrared emitters (IR) on one side of the room were paired with IR sensors containing speakers on the other side (as shown in FIG. 5A), to create an IR beam. If the movement of NOMAD 10 broke either IR beam, a tone was emitted by the speakers. Detection of the tone by NOMAD 10 elicited an orientation movement towards the source of the sound via the simulated nervous system 12.

Figure 6A:
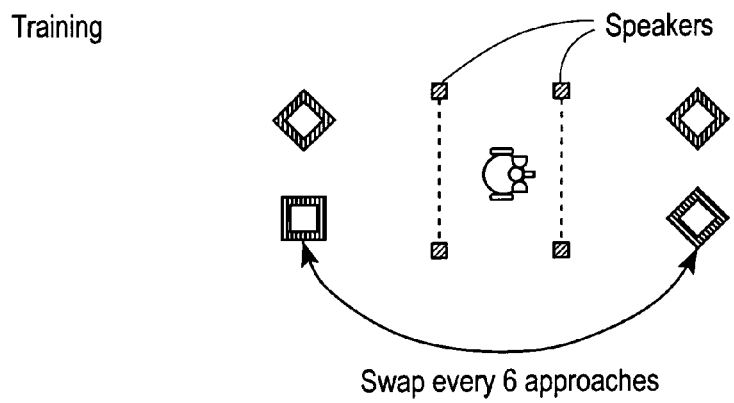
FIGS. 6A-6B are used to explain, respectively, the training and testing protocol of the brain-based device of FIGS. 1 and 2.
Figure 6B:
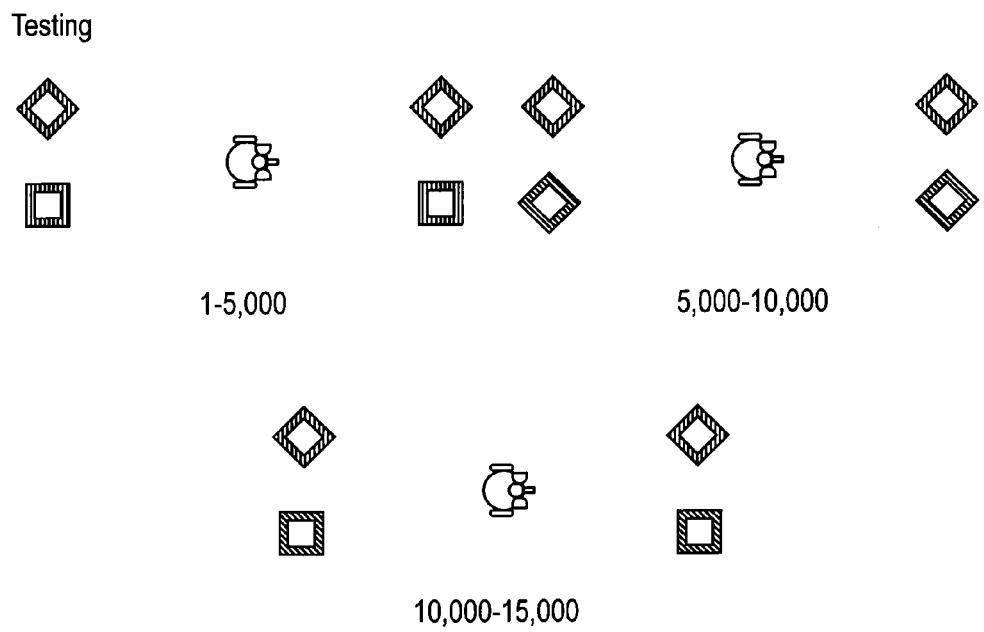

Experimental Protocol—FIGS. 6A-6B

FIGS. 6A and 6B illustrate the experimental set-up for NOMAD 10. NOMAD 10 views objects on two of the walls of an area, which is about "90 by 66". Experiments were divided into two stages, training and testing, as shown in FIGS. 6A and 6B, respectively. During both stages the activity and phase responses of all neuronal units of neural areas V1, V2, etc. were recorded for analysis.

During training as shown in FIG. 6A, NOMAD 10 explored its enclosure for 10,000 simulation cycles corresponding to roughly 24 approaches to the pairs of various objects shown. Responses to sounds emitted by the speaker (auditory cues) caused NOMAD 10 to orient toward the target, which in this example is the red diamond. The distracters, which were exchanged before every sixth approach to ensure that left-right orientation of NOMAD 10 did not confound target relation, are a green diamond and a red square. For testing, as shown in FIG. 6B, the speakers were turned off and NOMAD 10 was allowed to explore the environment for 15,000 simulation cycles. While the target object was continuously present for these 15,000 cycles, the distracters were changed every 5,000 cycles.

Training Stage Details—FIG. 6A

In the training stage shown in FIG. 6A, NOMAD 10 autonomously explored its enclosure for 10,000 simulation cycles, corresponding to 15-20 minutes of real time and approximately 24 approaches to the various pairs of visual shapes which were a red diamond and red square (on the left of FIG. 6A) and a red diamond and a green diamond (on the right of FIG. 6A). Thus, each pair contained a "target" shape (red diamond) and a "distracter" shape (green diamond on a red square). Distracters were deliberately designed to share attributes with the target, for example, when the red diamond was the target, a red diamond/red square pair was hung on one wall (shown on left side of FIG. 6A), and a red diamond/green diamond pair was hung on the other wall (shown on right side of FIG. 6A). The red diamond on either side of the room was closest to the speakers in both cases, as illustrated. To ensure that the left-right orientation of shapes in the target-distracter pair (e.g. red-square on the left, green-diamond on the right) did not confound target selection, the side of the distracters were exchanged every sixth viewing of a pair. During the training stage, responses to the speakers caused NOMAD 10 to orient towards the target.

Testing Stage Details—FIG. 6B

During testing, as shown in FIG. 6B, the speakers were turned off (therefore not shown), and NOMAD 10 was allowed to autonomously explore its enclosure for 15,000 simulation cycles. The first 10,000 cycles involved encounters with the same target and distracters present during the training stage of FIG. 6A. The final 5,000 cycles involved encounters with the target and the single shape of the set of four shapes (left and right) that did not share any features with the target (e.g. a pair consisting of a red diamond as target and a green square as distracter).

Training and testing were repeated with three different "subjects" of the brain-based device BBD using each of the four shapes as a target (a total of 12 training and testing sessions). Each BBD "subject" had the same physical device of NOMAD 10, but each possessed a unique simulated nervous system 24. This variability among "subjects" was a consequence of random initialization in both the microscopic details of connectivity between individual neuronal units and the initial connection strengths between those neuronal units. The overall connectivity among neuronal units remained similar among different "subjects", however, inasmuch as that connectivity was constrained by the synaptic pathways, arborization patterns, and ranges of initial connection strengths (see FIG. 2 and Table 2 for specifics).

Figures 7A, 7B:
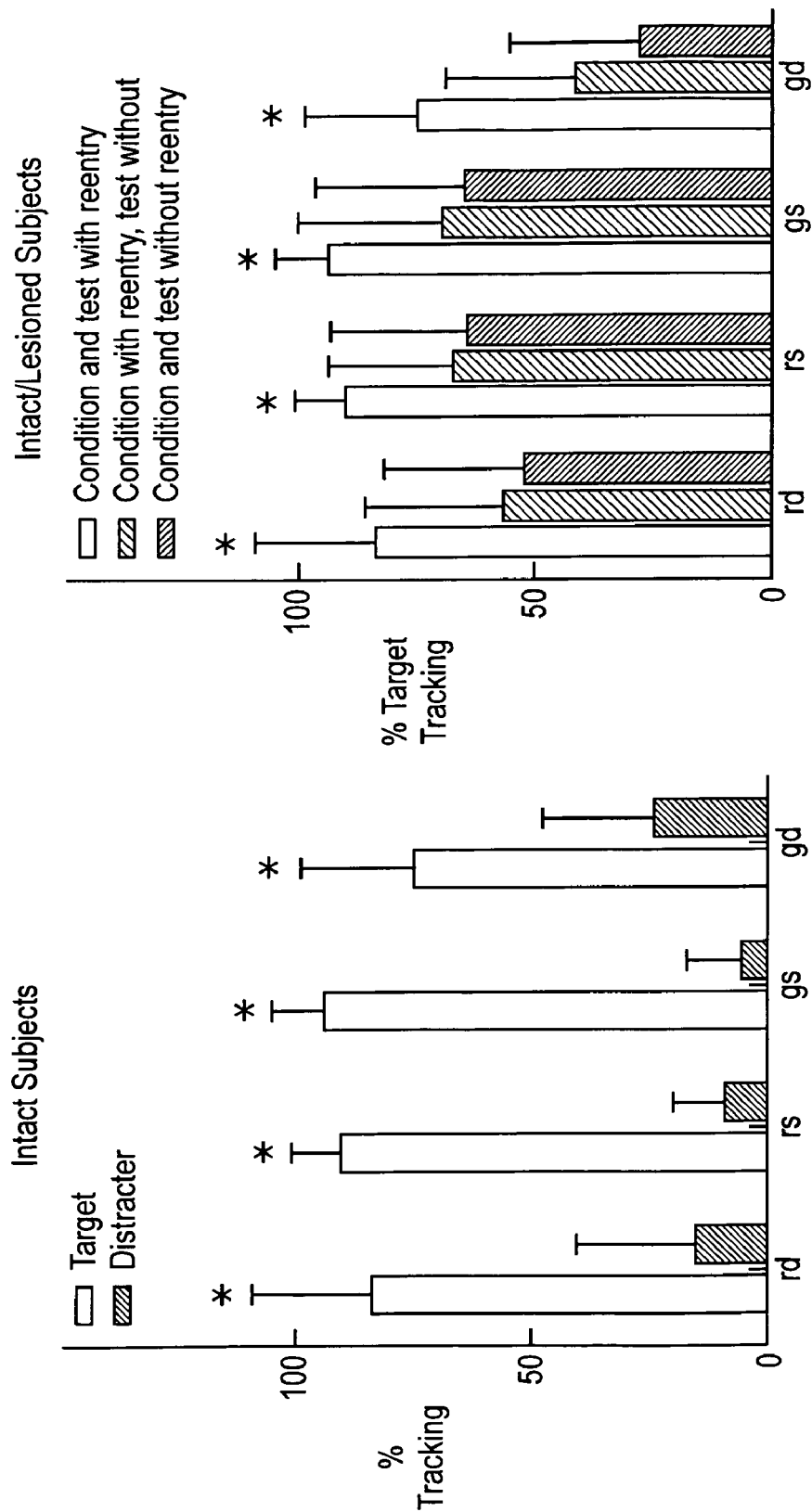
FIGS. 7A-7B are graphs illustrating the behavior of the brain-based device of FIGS. 1 and 2 following conditioning.

Target Tracking Behavior—Generally—FIGS. 7A-7B

The discrimination performance of each "subject" of the brain-based device BBD was assessed by how well that "subject" tracked toward target objects in the absence of auditory cues following conditioning or training, as shown in FIGS. 7A-7B. This was calculated as the fraction of time for which the target was centered in NOMAD 10's visual field via camera 16 during each approach to a pair of visual objects shown in FIG. 6B. Three separate "subjects" were conditioned to prefer one of four target shapes or objects, i.e. red diamond (rd), red square (rs), green square (gs) and green diamond (d). Activity in neural area V2 was used to assess the percentage of time for which the visual field of NOMAD 10 via its camera 16 was centered on a particular visual shape. Bars in the graphs of FIGS. 7A and 7B represent the mean percentage tracking time with error bars denoting the standard deviation. As shown in FIG. 7A, BBD "subjects" with intact reentrant connectors tracked the targets (white bars) significantly more than the distracters (gray bars) for each target shape, averaging overall approaches (*denote $p<0.01$ using a paired sample nonparameter sign test). As shown in FIG. 7B, "subjects" with reentrant connections intact (white bars) tracked targets significantly better than "subjects" with "lesions" only during testing (light gray bars), and subjects with lesions during both training and testing (black bars) (*denote $p<0.01$ using a RankSum test).

FIG. 7A shows that all "subjects" successfully tracked the four different targets over 80% of the time. This, despite the fact that the targets and distracters appeared in the visual field of camera 16 at many different scales and at many different positions as NOMAD 10 explored its environment (invariant object recognition described below). Moreover, NOMAD 10 achieved this process even though because of shared properties (e.g. same color or same shape), targets cannot be reliably distinguished from distracters on the basis of color or shape alone.

To investigate the importance of the presence of reentrant connections in the various "subjects" of the brain-based device BBD, certain inter-areal reentrant connections were lesioned at different stages of the experimental paradigm with the results shown in FIG. 7B. In one case, previously trained "subjects" were retested after lesioning. In a second case, reentrant connections were lesioned in both training and testing stages. Lesions were applied to a subset of inter-areal excitatory reentrant connections (see projections marked with an "X" in FIG. 2 and in Table 2), which had the effect of transforming the simulated nervous system 12 into a "feedforward" model of visual processing. To compensate for the reduction in activity due to these lesions, neuronal unit outputs in areas V2 and V4 were amplified (see Table 1). FIG. 7B shows that "subjects" with intact reentrant connections performed significantly better than either lesioned group. The decrease in performance observed in the absence of reentry connectors indicates that reentrant connections are essential for behavior, above chance, in the object discrimination task.

Figure 8:
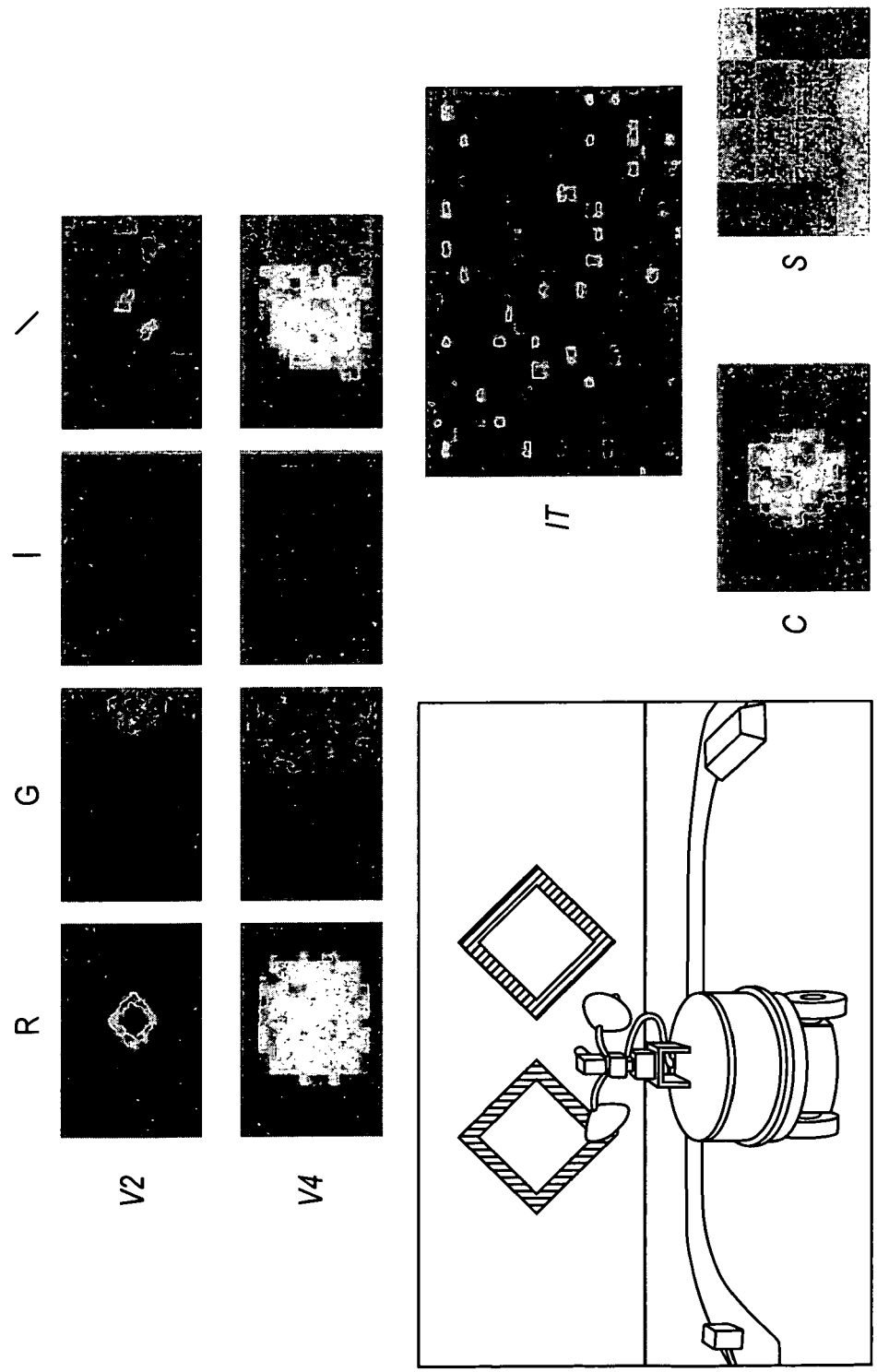
FIG. 8 is a snapshot of the neuronal unit activity of the brain-based device of FIGS. 1 and 2 during a behavioral experiment.

Neural Dynamics During Behavior—FIG. 8

During the behavior of NOMAD 10 in its environment, circuits comprised of synchronously active neuronal groups were distributed throughout different neural areas in the simulated nervous system 12. Multiple objects in the environment were distinguishable by the differences in phase between the corresponding active circuits. A snapshot of the neural responses during a typical behavioral run is given in FIG. 8. This snapshot shows NOMAD 10 during an approach to a red diamond target and a green diamond distracter towards the end of a training session (FIG. 6A). Each pixel in the depicted neural areas V2, V4, IT, C and S represents the activity and phase of a single neuronal unit within the respective given neural area. Thus, for example, FIG. 8 shows the responses for neural areas V2 and V4 specifically their neural sub-areas in color (red, green) and line orientation (vertical, diagonal). The phase is indicated by the color of each pixel and the activity is indicated by brightness of the pixel (black is no activity; very bright is maximum activity).

FIG. 8 shows two neural circuits which are differentiated by their distinct phases and which were elicited respectively by the red diamond and the green diamond stimuli. As shown in the figure, NOMAD 10 has not yet reached the IR beam that triggers the speakers in its environment to emit a tone (see FIG. 6A). The activity of neural area S (the value system) was nonetheless in phase with the activity in neural areas V2 and V4 corresponding to the target, and was therefore predictive of the target's saliency or value. Area IT has two patterns of activity, indicated by the two different phase colors, which reflect two perceptual categories. These patterns were brought about by visual input from camera 16 that is generated during the movement of NOMAD 10 in this environment. Finally, neural area C has more activity on the side that facilitates orientation of NOMAD 10 towards the target (i.e. the red diamond).

Figure 9A:
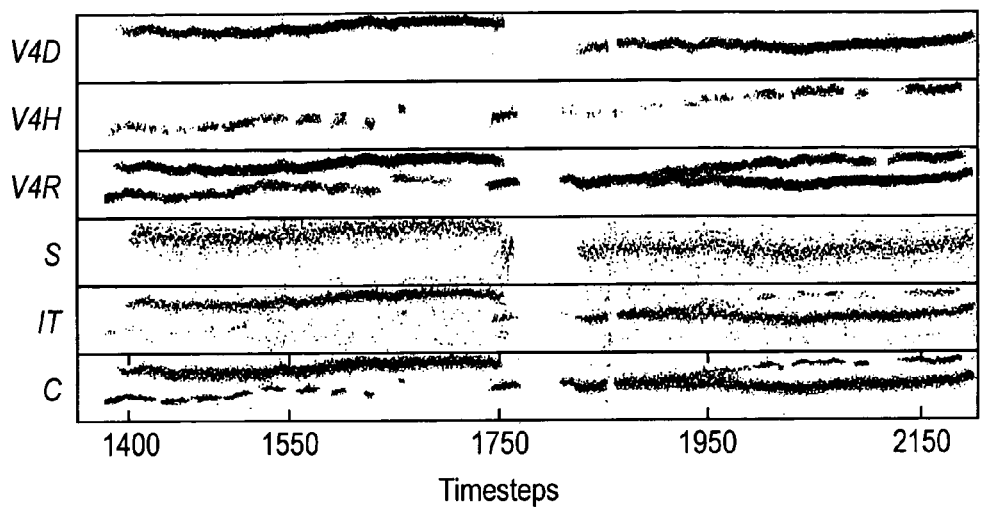
FIGS. 9A-9B show phase responses with and without reentry connections, respectively, of the brain-based device of FIGS. 1 and 2 following conditioning.
Figure 9B:
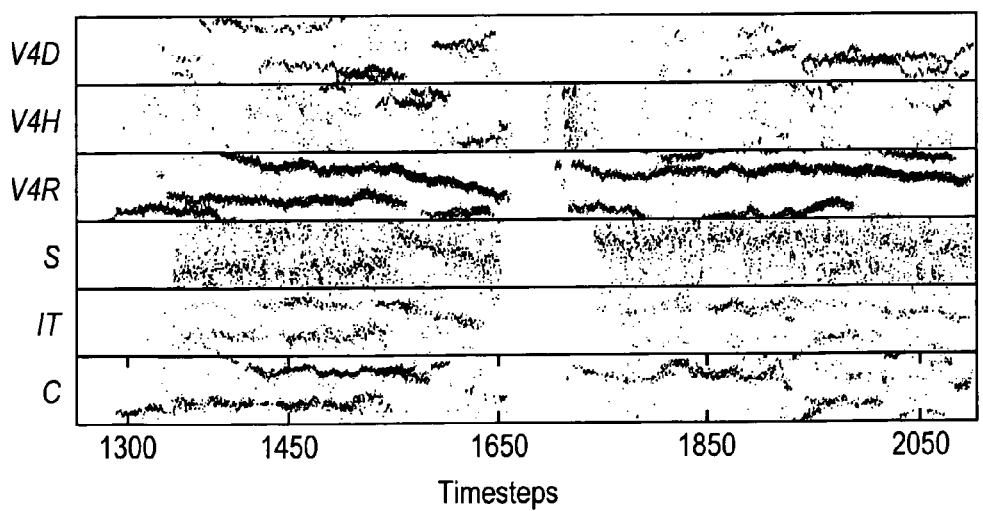

Dynamics of Neural Responses—FIGS. 9A and 9B

To analyze the dynamics of these neural responses, the phase distributions of active neuronal units during approaches to target-distracter pairs in the testing sessions were examined. FIG. 9A shows the distribution of neuronal phases in various neural areas during approaches to a red diamond target in the presence of a red square distracter, by an intact "subject" (with reentrant connections). FIG. 9A shows consistent correlations among phase distributions in neural sub-areas V4R (red), V4H (horizontal), and V4D (diagonal). The bimodal distribution in neural sub-area V4R reflects the presence of two red shapes (diamond, square) in the environment of NOMAD 10: one trace correlates reliably with neural sub-area V4D (diagonal) and can therefore be associated with the red diamond, the other correlates reliably with sub-area V4H (horizontal) and can be associated with the red square (not shown is area V4G which remained inactive during this period). The phases of the active neuronal units in areas S, IT, and C were strongly correlated with the red diamond target, as opposed to the red square distracter, reflecting the synaptic changes brought about by previous conditioning during the testing phase to prefer the red diamond. The global pattern of network activity thus displayed a biased phase distribution in favor of the target.

Quantification of Biased Phase Distribution—FIGS. 9A-9B; Table 3

To quantify this bias and assess its generality, the proportion of neuronal units in areas S, IT, and C associated with the target with the proportion associated with the distracter during the testing. Table 3 shows average values of these proportions calculated over all "subjects" and all four target shapes.

TABLE 3

Neuronal composition and average activity of functional circuits corresponding to target and distracter objects.

| Area | % units responding to target | % units responding to distracter | mean firing rate of units responding to target | mean firing rate of units responding to distracter |
|---|---|---|---|---|
| S | 61.25 (17.78)* | 10.34 (4.88) | 0.537 (0.089) | 0.495 (0.080) |
| IT | 4.29 (0.495)* | 2.91 (0.366) | 0.579 (0.064)* | 0.467 (0.015) |
| C | 19.04 (1.45)* | 10.80 (1.93) | 0.626 (0.062)* | 0.398 (0.032) |
| V4 | 14.83 (0.833)* | 11.61 (0.819) | 0.829 (0.003)* | 0.823 (0.002) |

A significantly greater proportion of neuronal units were part of functional circuits associated with targets than in circuits associated with distracters. In addition, those neuronal units associated with targets had significantly higher firing rates than neuronal units in circuits associated with distracters.

The above shows that perceptual categorization and visual object discrimination by NOMAD 10 is enabled by the coherent interaction of local and global neuronal circuit processes, as mediated by reentrant connections, of simulated nervous system 12. Local processes correspond to activity in each neural area, whereas global processes correspond to the distinct, but distributed functional circuits that emerged throughout the simulated nervous system 12. These interactions are evident in FIG. 9A, in which activity in each of the local areas strongly reflects the global bias in favor of the red-diamond target (see also Table 3).

The Influence of Reentry on Neural Dynamics

Lesioning of reentrant connections interfered significantly with interactions between the local and global processes mentioned above. Even in a very simple network model, removal of reentrant connections can prevent the emergence of neural synchrony (see FIGS. 3A-3E). On a larger scale, FIG. 9B shows approaches by the same NOMAD 10 "subject" depicted in FIG. 9A to the same target/distracter pair, following lesions of inter-areal excitatory reentrant connections. While some individual areas continued to show peaks in their phase distribution (e.g. neural sub-area V4R), many do not, and the phase correlations between the neural areas are severely diminished. This occurred not only among the various V4 neural areas (FIG. 2), but also among area V4 and areas S, IT, and C. The dynamically formed and globally coherent circuits, which were clearly evident in the intact "subject", were almost entirely absent in the lesioned "subjects". For example, FIG. 9B shows that activity in area S no longer correlates uniquely with a single trace in area V4; instead, it alternates between two distinct states. The absence of a dominant trace in neural areas IT and C is also shown.

Phase correlations between neural areas were significantly higher for "subjects" with intact reentrant connections than for "subjects" in either lesion group. The overall median rank correlation coefficient was 0.36 for the intact "subjects", 0.21 for the "subjects" with lesions only during the test stage, and 0.17 for the "subjects" with lesions in both the training and test stages. Also, "subjects" with lesions only during testing had significantly higher correlation coefficients than "subjects" with lesions during both training and testing. This reflects the contribution of reentrant connections to the formation of global circuits during training (FIG. 6A). All of these findings are consistent with the drop in behavioral performance in the absence of reentrant connections (see FIG. 7).

Figures 10A, 10B, 10C:
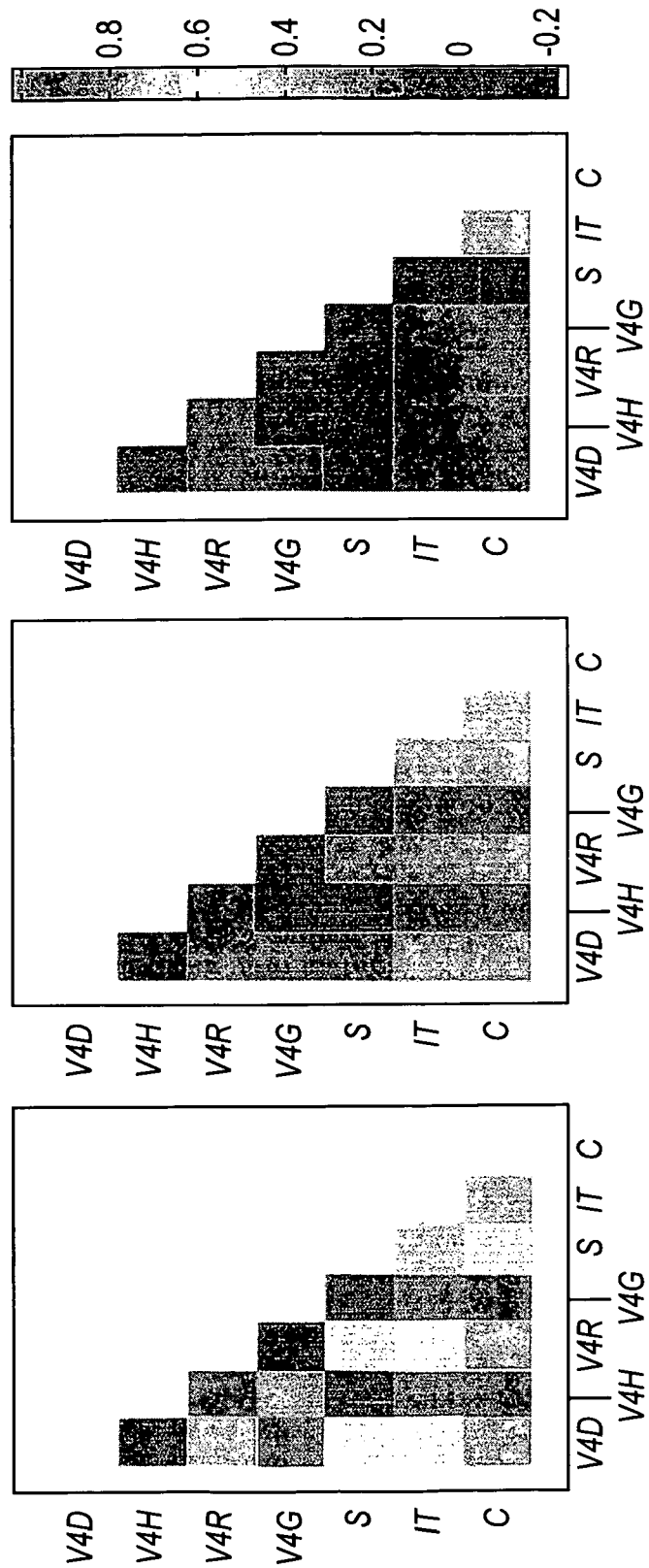
FIGS. 10A-10C are used to explain phase correlations among neural areas for the brain-based device of FIGS. 1 and 2 conditioned to prefer or discriminate a red diamond as a single target object.

Phase Correlations Among Neural Areas—Single "Subject" Conditioned to a Red Diamond Shape FIGS. 10A-10C illustrate geographically a representative example of the correlation of phases among neural areas for a "subject" after conditioning to prefer red diamond targets. The figures are color coded (dark blue denotes no correlation, dark red denotes high correlation), and each colored area shows the correlation coefficient between the mean phases of a given pair of neural areas. FIG. 10A shows correlation coefficients when reentrant connections were intact. In agreement with the data shown in FIG. 9, strong phase correlations were found between areas associated with specific target features (V4D and V4R), and among these areas and areas S, IT and C. The correlations among neural areas for the same "subject" with reentrant connections lesioned during testing (FIG. 10B) and with reentrant connections lesioned during both conditioning and testing (FIG. 10C) were both considerably weaker. As graphically indicated, the connections between neural areas V1, V2, etc. associated with the target are considerably higher with reentrant connections intact (FIG. 10A) than in either lesion case (FIGS. 10B and 10C).

Figure 11A:
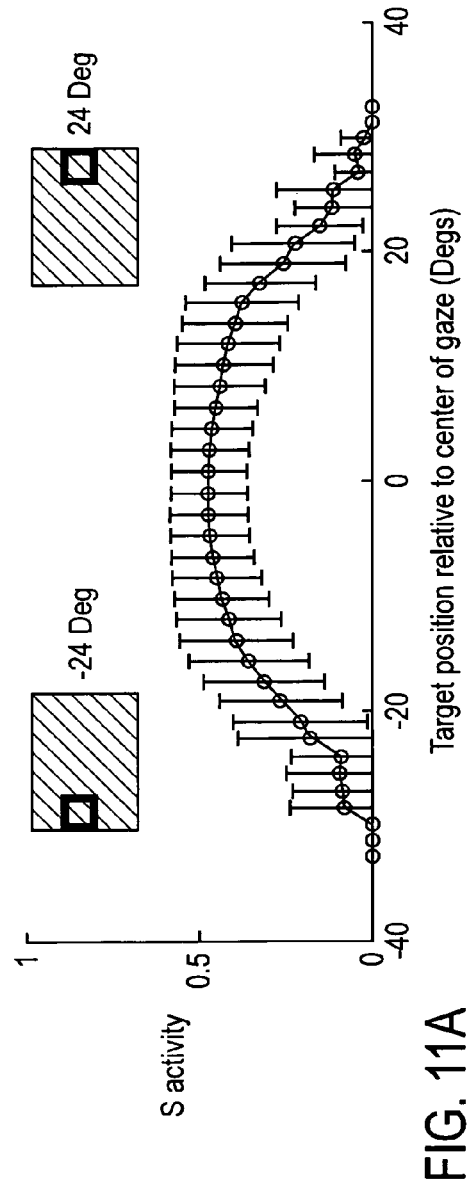
FIGS. 11A-11B are illustrations used to explain the response of the neural value area S to target objects in different real-world positions and at different scales.
Figure 11B:
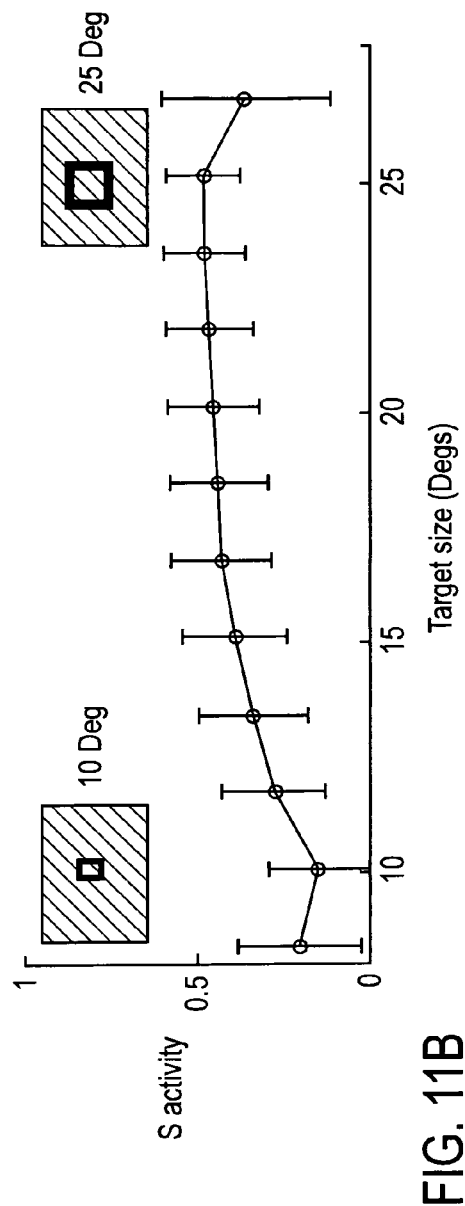

Invariant Object Recognition—FIGS. 11A and 11B

FIGS. 11A and 11B are graphs illustrating the response of neural value area S to target objects in the visual field of NOMAD 10 at different positions and at different scales. Average values were calculated for all approaches by NOMAD 10 "subjects" to all target objects, with the error bars indicating standard errors. FIG. 11A shows average responses as a function of target position within the visual field (135°). FIG. 11B shows average responses as the apparent target size ranged from 8° to 27° of visual angle. The insets in FIGS. 11A and 11B indicate how the square target appears in NOMAD 10's field of view at extreme positions and scales.

Because images of the visual objects varied considerably in size and position as NOMAD 10 explored its enclosure, successful discrimination required invariant object recognition. In order to analyze this capacity, the value system, i.e. neural area S, was examined which, after conditioning, responded preferentially to target objects over distracters due to plasticity in the pathway IT→S. In a typical approach, as NOMAD 10 moved from one side of the environment to the other, neural area S responded briskly and in phase with neuronal units in areas V2, V4, and IT corresponding to attributes of the target. Calculating average values overall "subjects" and all target shapes, it was found that area S responded reliably to target images which appeared within 120° of the center of the field of view (the range of the visual field was approximately ±35°) and as the apparent target size ranged from 8° to 27° of visual angle. Thus, the object recognition of the brain-based device BBD of the present invention while autonomously moving in its environment was both position and scale invariant.

Figures 12A, 12B:
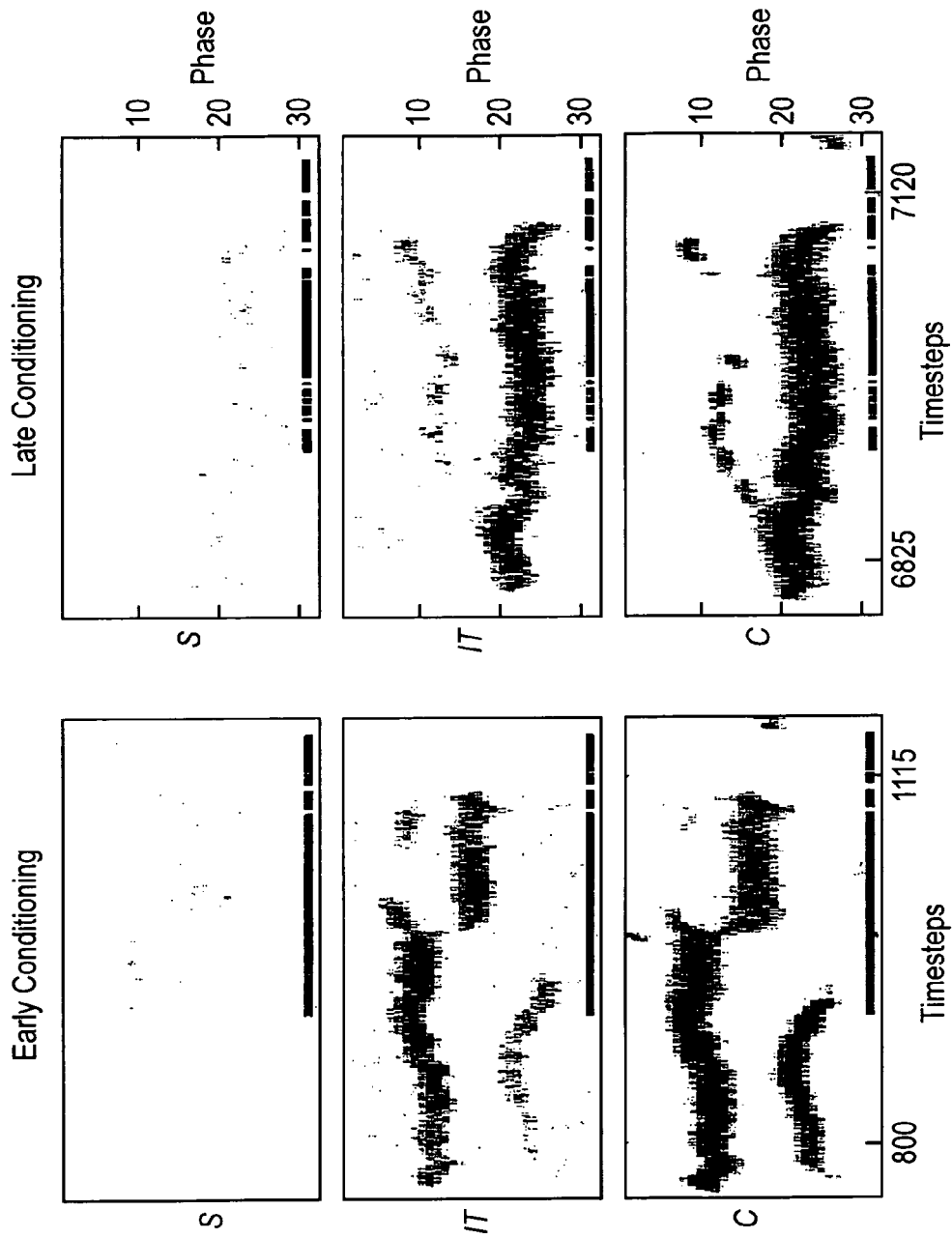
FIGS. 12A-12B show neural activity during conditioning or training of the brain-based device of FIGS. 1 and 2 for neural areas S, IT and C.

Value System (Neural Area S) Activity During Conditioning—FIGS. 12A and 12B

Neural activity during conditioning for a single "subject", for neural areas S, IT, and C during a single approach to a target shape is shown in FIG. 12A, at an early stage (left panels, time steps 750-1165), and in FIG. 12B, at a late stage of conditioning (right panels, time steps 6775-7170). Each panel shows the distribution of neuronal unit phases in the corresponding neural area over time. As in FIGS. 9A and 9B, a gray scale indicates the proportion of neuronal units in each neural area at a particular phase. The solid line at the bottom of each panel indicates time steps for which the tone from a speaker was present (see FIG. 6A). In the early conditioning training period (left panels) area S is inactive until tone onset, i.e. an audible activity, at which point it becomes strongly activated in phase with the upper traces in both areas IT and C, which are associated with the target. The lower traces in areas IT and C, corresponding to the distracter, become relatively suppressed at the same time. Later in conditioning (right panels), areas S, IT and C are in phase with visual system activity corresponding to the target (lower trace) well before tone onset, and activity associated with the distracter is relatively suppressed well before the tone onset.

As a result of value-dependent synaptic plasticity during conditioning (i.e. the plasticity of the synaptic connectors are dependent on value), the visual attributes of target objects became predictive of value. As shown in FIG. 12A, during early conditioning area S does not become active until the UCS (unconditioned stimulus; i.e. the tone) is present. The UCS also evokes biases in areas IT and C, as shown by the rapid abolition of the initially bimodal phase distributions in these areas.

At a later stage of conditioning, the CS (the conditioned stimulus; i.e. the target visual features) has become associated with value such that activity in area S now precedes UCS onset (see FIG. 12B). Area S responds to the target stimulus as soon as the stimulus appears in NOMAD 10's visual field. Activity in area S then facilitates a bias in areas IT and C, as shown in FIGS. 12A-12B by the appearance of a single phase distribution peak in each area well before UCS onset. This shift in the timing of value-related activity, from activity triggered by the auditory UCS in early trials (i.e. auditory input provides value), to activity triggered by the visual CS in later trials (i.e. visual input now provides value), is analogous to the shift in dopaminergic neural activity found in the primate ventral tegmental area during conditioning. Value-dependent synaptic plasticity is also similar to "temporal-difference" learning in that the conditioned stimulus becomes predictive of value.

Computer System and Flow Charts

Figure 13:
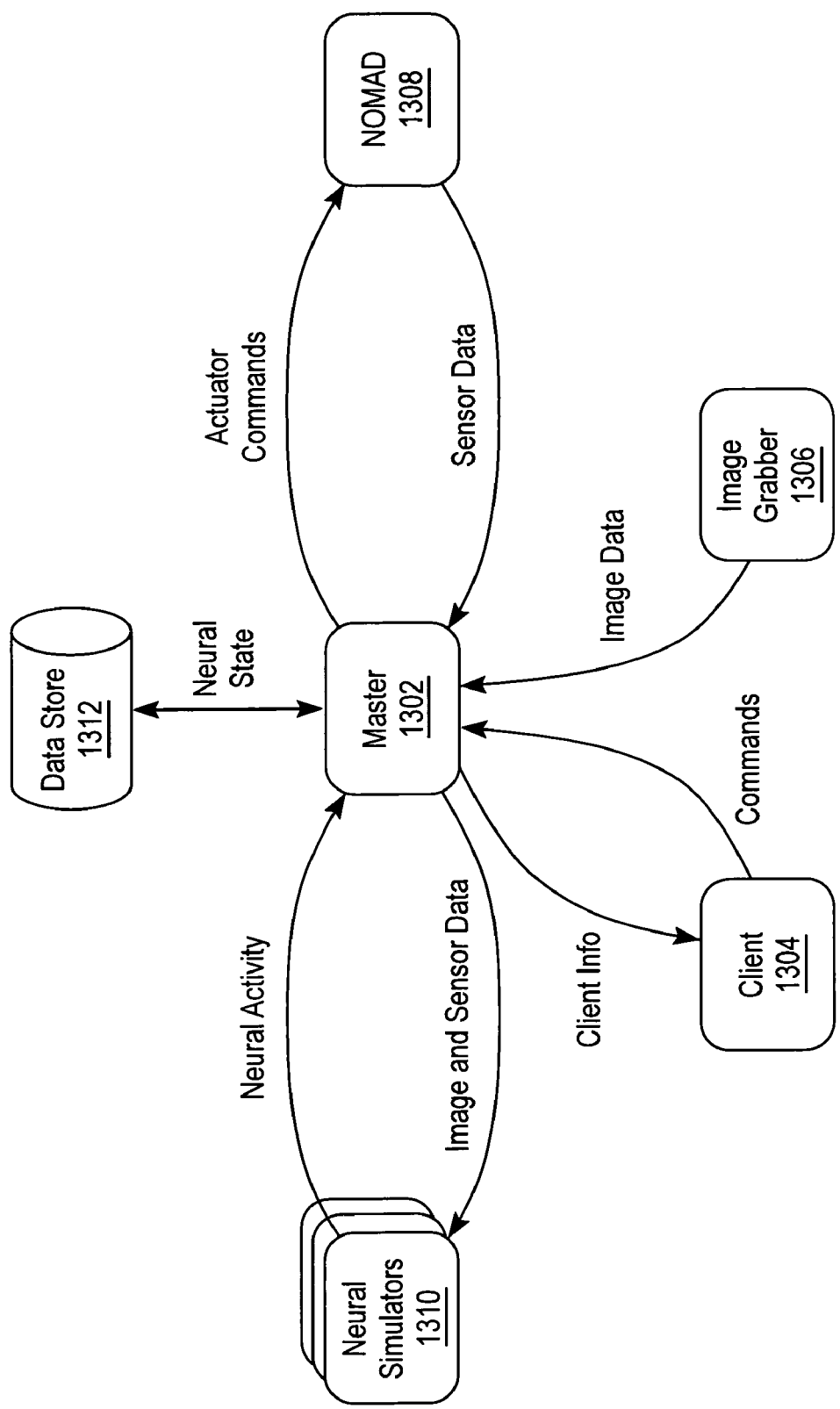
FIG. 13 is an exemplary illustration of a system in accordance with various embodiments of the invention.

FIG. 13 is an exemplary illustration of a system in accordance with various embodiments of the invention. Although this diagram depicts components as logically separate, such depiction is merely for illustrative purposes. It will be apparent to those skilled in the art that the components portrayed in this figure can be arbitrarily combined or divided into separate software, firmware and/or hardware components. Furthermore, it will also be apparent to those skilled in the art that such components, regardless of how they are combined or divided, can execute on the same computing device or can be distributed among different computing devices connected by one or more networks or other suitable communication means.

In various embodiments, the components illustrated in FIG. 13 can be implemented in one or more programming languages (e.g., C, C++, Java™, and other suitable languages). Components can communicate using Message Passing Interface (MPI) or other suitable communication means, including but not limited to shared memory, distributed objects and Simple Object Access Protocol (SOAP). MPI is an industry standard protocol for communicating information between computing devices (or nodes). In one embodiment, the system can be deployed on a multi-processor computer architecture such as (but not limited to) a Beowulf cluster. Beowulf clusters are typically comprised of commodity hardware components (e.g., personal computers running the Linux operating system) connected via Ethernet or some other network. The present disclosure is not limited to any particular type of parallel computing architecture. Many other such architectures are possible and fully within the scope and spirit of the present disclosure.

Referring to FIG. 13, master component 1302 can coordinate the activities of the other components according to commands received from client 1304. In one embodiment, the client can be a stand-alone process that programmatically controls the master according to a script or other scenario and/or in reaction to client information (e.g., neural activity, sensor readings and camera input) received from the master. Client commands can instruct the master to start or stop the brain-based device BBD experiment, save the experiment state on data store 1312, read the experiment state from the data store, set the running time/cycles in which the experiment will execute, and set parameters of the neural simulators 1310.

In another embodiment, the client can be a user interface that receives information from the master and allows a user to interactively control the system. By way of a non-limiting example, a user interface can include one or more of the following: 1) a graphical user interface (GUI) (e.g., rendered with Hypertext Markup Language); 2) an ability to respond to sounds and/or voice commands; 3) an ability to respond to input from a remote control device (e.g., a cellular telephone, a PDA, or other suitable remote control); 4) an ability to respond to gestures (e.g., facial and otherwise); 5) an ability to respond to commands from a process on the same or another computing device; and 6) an ability to respond to input from a computer mouse and/or keyboard. This disclosure is not limited to any particular UI. Those of skill in the art will recognize that many other user interfaces are possible and fully within the scope and spirit of this disclosure.

The neuronal units for each neural area (e.g., V1, V2, V4, IT, C, S, Mic-left, A-left, Mic-right, A-right) are each assigned to a neural simulator 1310. Each neural simulator 1310 is responsible for calculating the activity of the neuronal units that have been assigned to it. A given neural area's neuronal units may be distributed across one or more neural simulators 1310. In various embodiments, there can be one neural simulator per Beowulf node. In order to optimize performance, neuronal units can be distributed among neural simulators such that the average number of synaptic connections on the neural simulators is approximately the same. In other embodiments, neuronal units can be distributed such that the average number of neuronal units per neural simulator is approximately the same. Neural simulators periodically or continuously exchange the results of calculating the activity of their neuronal units with other neural simulators and the master. This information is required so that neuronal units on other neural simulators have up-to-date pre-synaptic inputs. The master provides actuator commands to the NOMAD based on the neural activity received from the neural simulators.

The master periodically receives image data from image grabber 1306 and distributes it to the neural simulators and to the client. In one embodiment, the images are taken from the CCD camera 16 mounted on NOMAD 10 that sends 320×240 pixel RGB video images, via an RF transmitter, to an ImageNation PXC200 frame grabber. The image is then spatially averaged to produce an 80×60 pixel image. Gabor filters can be used to detect edges of vertical, horizontal, and diagonal (45 and 135 degrees) orientations (as briefly described above). The output of the Gabor function is mapped directly onto the neuronal units of the corresponding V1 sub-area. Color filters (red positive center with a green negative surround, or red negative center with a green positive surround) are also applied to the image. The outputs of the color filters are mapped directly onto the neuronal units of V1-Red and V1-Green. V1 neuronal units projected retinotopically to neuronal units in neural area V2.

The master component also periodically acquires sensor data from NOMAD 10 component 1308 and distributes it to the neural simulators. In one embodiment, a micro controller (PIC17C756A) onboard the NOMAD 10 samples input and status from its sensors and controls an RS-232 communication between the NOMAD base and master. Sensor information can include, in addition to video and audio information previously described, gripper state, camera position, infrared detectors, whisker deflection, wheel speed and direction, odometer count, and microphone input. In one embodiment, a root mean square (RMS) chip measures the amplitude of the microphone input signal and a comparator chip produces a square waveform which allows frequency to be measured. A micro controller on NOMAD 10 periodically calculates the overall microphone amplitude by averaging the current signal amplitude measurement with the previous three measurements. The micro controller calculates the frequency of the microphone signal at each time point by inverting the average period of the last eight square waves. Neural areas Mic-left and Mic-right respond to tones between 2.9 and 3.5 kHz having an amplitude of at least 40% of the maximum. The activity of a neuronal unit in neural area Mic-left or Mic-right is given by $$s_i^{mic}(t+1)=\tan h(0.9 s_i^{mic}(t)+0.1 a_i^{mic}),$$

where $s_i^{mic}(t)$ is the previous value of a neuronal unit i in Mic-left or Mic-right, and $a_i^{mic}$ is the current amplitude of the microphone output.

Figure 14:
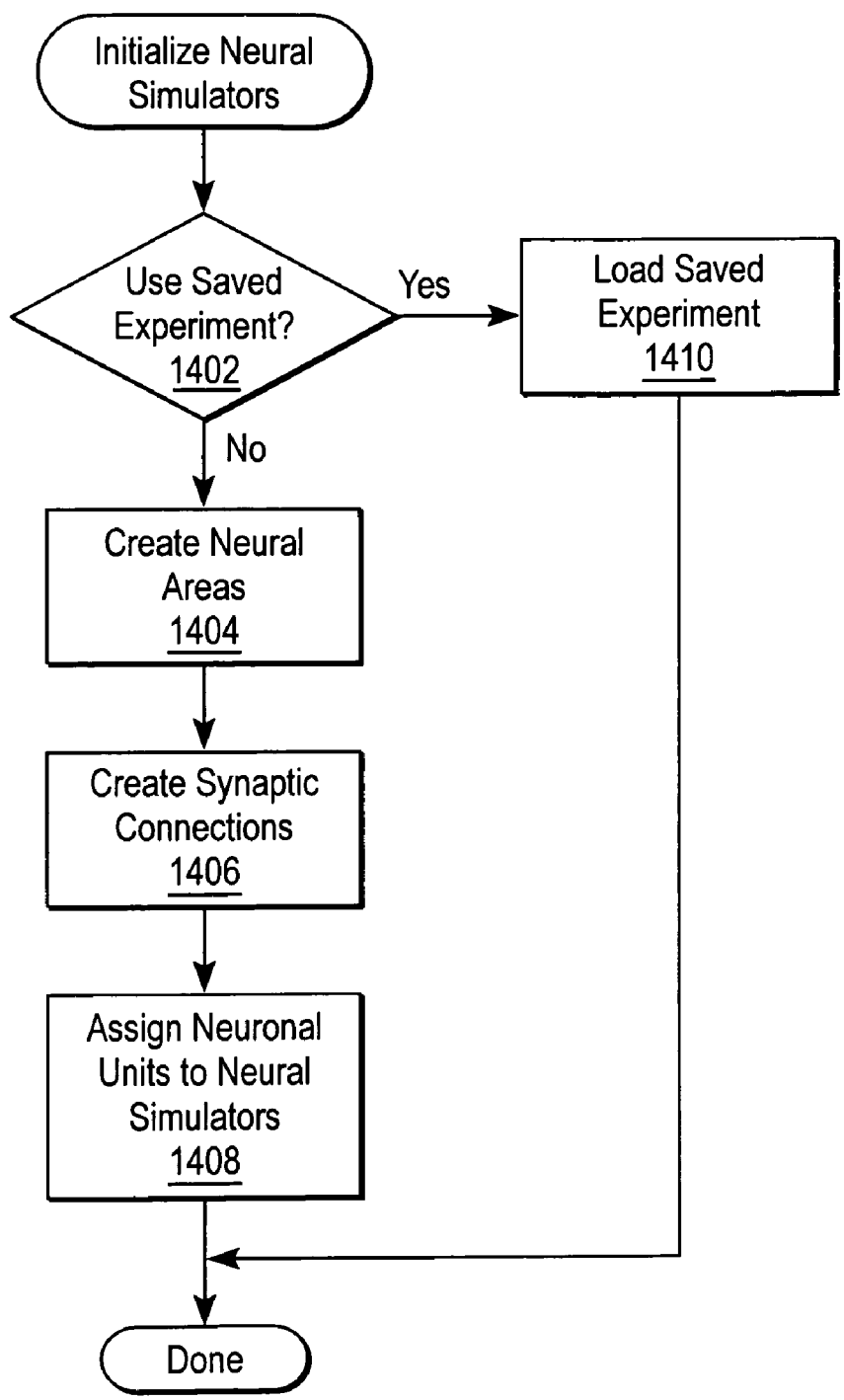
FIG. 14 is a flow diagram illustration of neural simulator initialization.

FIG. 14 is a flow diagram illustration of neural simulator initialization in accordance with various embodiments of the invention. Although this figure depicts functional steps in a particular order for purposes of illustration, the process is not necessarily limited to any particular order or arrangement of steps. One skilled in the art will appreciate that the various steps portrayed in this figure can be omitted, rearranged, performed in parallel, combined and/or adapted in various ways. In step 1402, it is determined based on command(s) from the client 1304 whether or not a saved experiment should be retrieved from the data store 1312 or whether a new experiment should be started. If the experiment is to be retrieved from the data store, this is performed in step 1410. In various embodiments, the experiment state can be stored as an Extensible Markup Language (XML) document, a plain text file, or a binary file. Otherwise, in step 1404 neuronal units are created according to the parameters given in Table 1. Next, in step 1406 synaptic connections are created between the neuronal units according to the parameters in Table 2. Finally, each neuronal unit is assigned to a neural simulator in step 1408.

Figure 15:
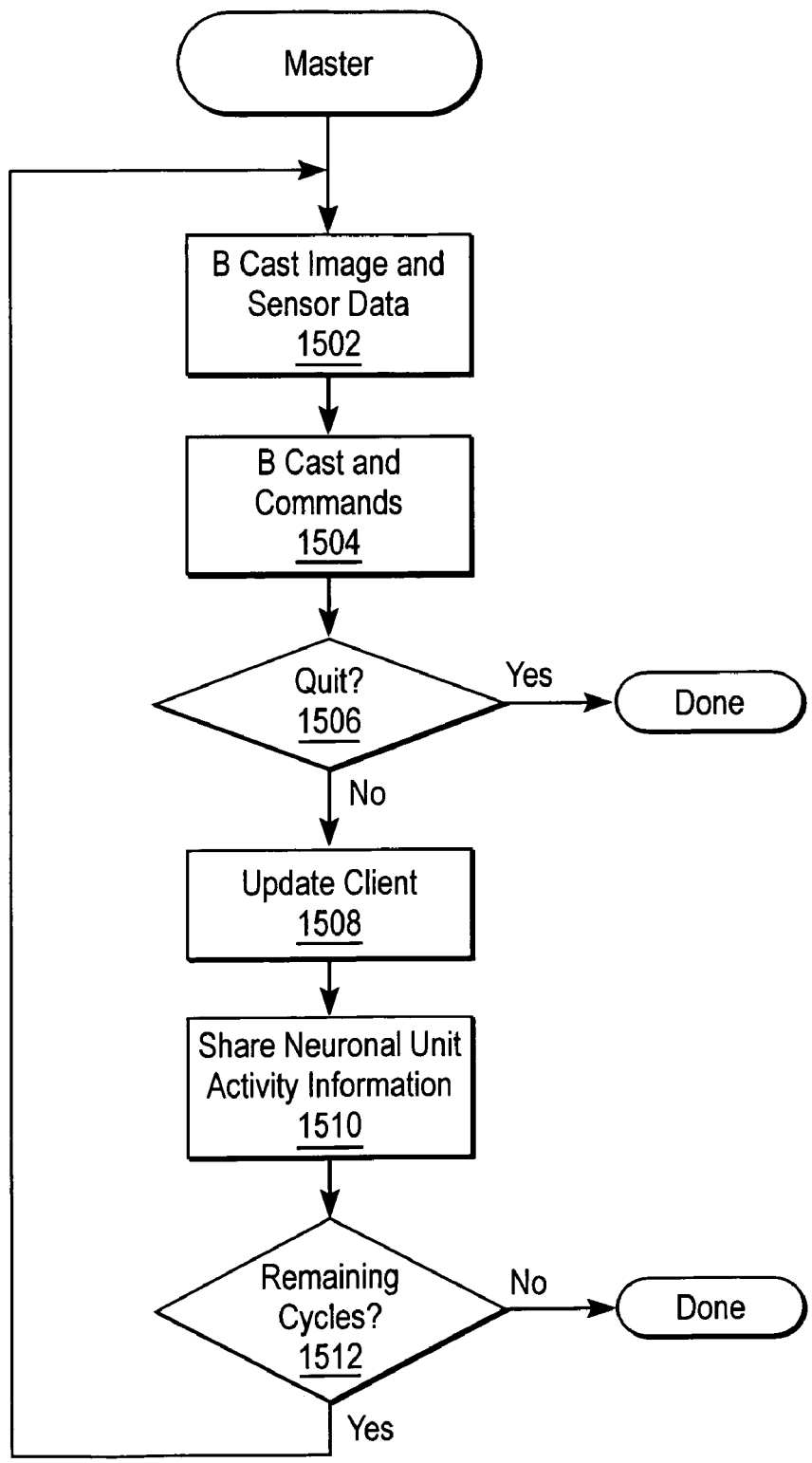
FIG. 15 is a flow diagram illustration of the master component in accordance with various embodiments of the invention.

FIG. 15 is a flow diagram illustration of the master component in accordance with various embodiments of the invention. Although this figure depicts functional steps in a particular order for purposes of illustration, the process is not necessarily limited to any particular order or arrangement of steps. One skilled in the art will appreciate that the various steps portrayed in this figure can be omitted, rearranged, performed in parallel, combined and/or adapted in various ways.

In step 1502 the master broadcasts image and sensor data that it has acquired from the image grabber and NOMAD 10 to the neural simulators and the client. In step 1504, the master broadcasts any commands it may have received to the neural simulators. In step 1506, it is determined whether or not the client has directed the master to quit the experiment. If so, the master ceases the experiment (which may include saving the state of the experiment to the data store). Otherwise, in step 1508 the updated information is provided to the client which could serve to update a GUI. In step 1510, neuronal unit activity from the neural simulators is shared among all components (e.g., via MPI). The neuronal activity can be provided in some form to the client as part of the client information. Finally, it is determined whether or not there are any remaining cycles left in the simulation. If not, the experiment terminates. Otherwise, the master returns to step 1502.

Figure 16:
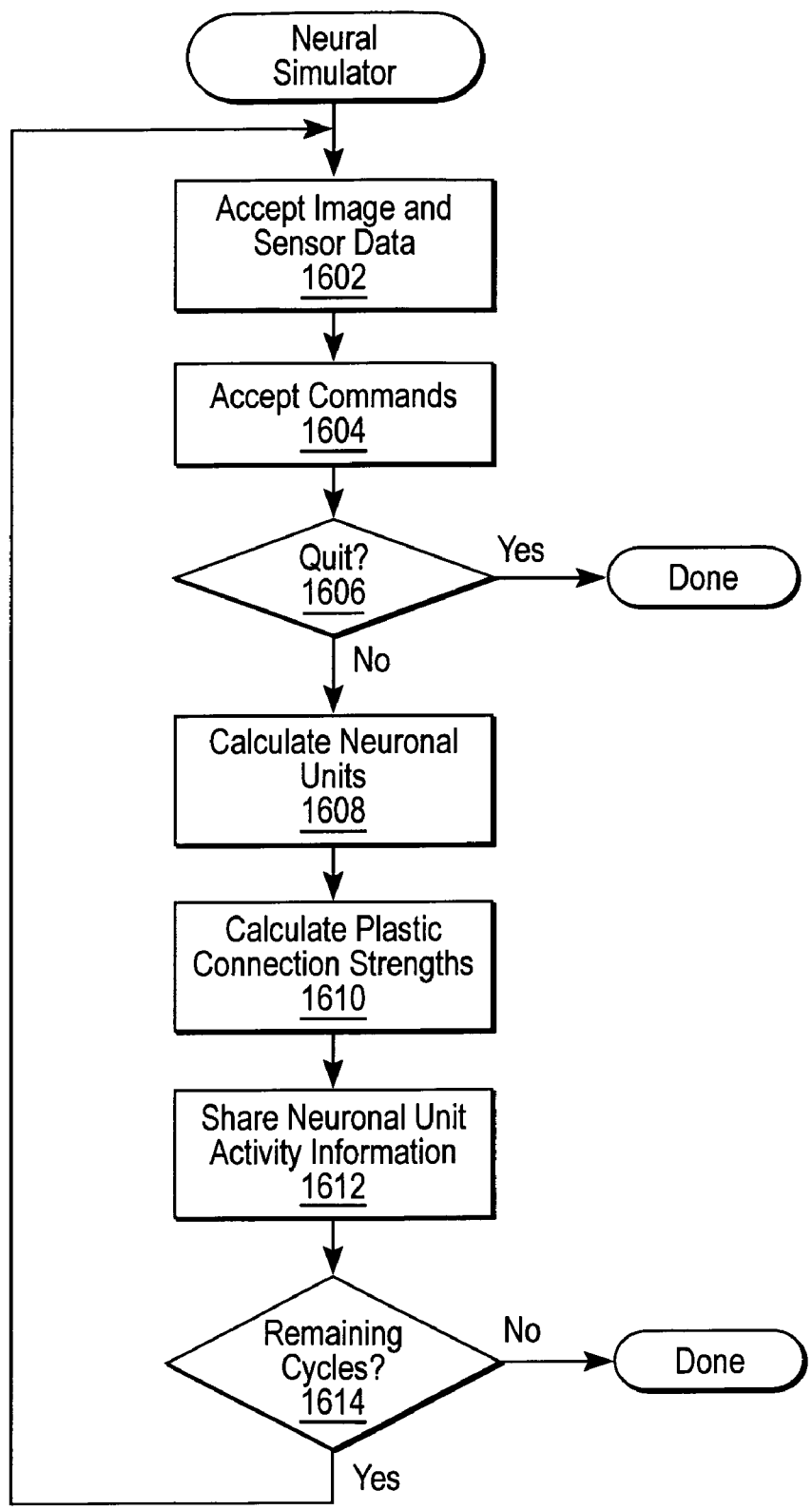
FIG. 16 is a flow diagram illustration of a neural simulator in accordance with various embodiments of the invention.

FIG. 16 is a flow diagram illustration of a neural simulator in accordance to various embodiments of the invention. Although this figure depicts functional steps in a particular order for purposes of illustration, the process is not necessarily limited to any particular order or arrangement of steps. One skilled in the art will appreciate that the various steps portrayed in this figure can be omitted, rearranged, performed in parallel, combined and/or adapted in various ways.

In step 1602, the neural simulator accepts image and sensor data that is broadcast by the master. In step 1604, client commands broadcast by the master are accepted. In step 1606, it is determined whether or not the client has directed the master to quit the experiment. If so, the neural simulator completes its execution. Otherwise, in step 1608 the value of the neuronal units assigned the neural simulator are calculated. In step 1610, the strengths of plastic connections are calculated. Local neuronal unit activity is shared in step 1612 with other neural simulators and the master. In addition, neuronal activity from other neural simulators is acquired and used to refresh local values. Finally, it is determined in step 1614 whether or not there are any remaining cycles left in the simulation. If not, the experiment terminates. Otherwise, the neural simulator returns to step 1602.

Various embodiments may be implemented using a conventional general purpose or a specialized digital computer or microprocessor(s) programmed according to the teachings of the present disclosure, as will be apparent to those skilled in the computer art. Appropriate software coding can readily be prepared by skilled programmers based on the teachings of the present disclosure, as will be apparent to those skilled in the software art. The invention may also be implemented by the preparation of integrated circuits or by interconnecting an appropriate network of conventional component circuits, as will be readily apparent to those skilled in the art.

Various embodiments include a computer program product which is a storage medium (media) having instructions stored thereon/in which can be used to program a general purpose or specialized computing processor/device to perform any of the features presented herein. The storage medium can include, but is not limited to, one or more of the following: any type of physical media including floppy disks, optical discs, DVDs, CD-ROMs, microdrives, magneto-optical disks, ROMs, RAMs, EPROMs, EEPROMs, DRAMs, VRAMs, flash memory devices, magnetic or optical cards, nanosystems (including molecular memory ICs); and any type of media or device suitable for storing instructions and/or data. Various embodiments include a computer program product that can be transmitted over one or more public and/or private networks wherein the transmission includes instructions which can be used to program a computing device to perform any of the features presented herein.

Stored one or more of the computer readable medium (media), the present disclosure includes software for controlling both the hardware of the general purpose/specialized computer or microprocessor, and for enabling the computer or microprocessor to interact with a human user or other mechanism utilizing the results of the present invention. Such software may include, but is not limited to, device drivers, operating systems, execution environments/containers, and applications.

SUMMARY

A brain-based device (BBD), including NOMAD 10 controlled by a simulated nervous system 12 has been discussed, which bound the visual attributes of distinct stimuli. Binding in the brain-based device BBD occurred as a result of multi-level interactions involving a reentrant neuroanatomy (FIG. 2, Table 1 and Table 2), the dynamic synchronization of neuronal groups, and the correlations generated by synaptic plasticity and autonomous behavior of NOMAD 10 moving in its environment. Specifically, during approaches to visual objects the formation of synchronously active neuronal circuits occurred for each object in the visual field of NOMAD 10. These circuits, which were enabled by reentrant connections within and among neural areas V1, V2, etc., gave rise to motor area activity which in turn evoked discriminatory behavior of NOMAD 10. This provides insight into the complex, dynamic interactions between brain, body, and behavior that underlie effective visual object recognition.

The brain-based device BBD of the present invention has innately specified behavior (i.e. tracking towards auditory or visual stimuli) and innately specified value or salience for certain environmental signals (e.g. positive value of sound). The BBD learned autonomously to associate the value of the sound with the attributes of the visual stimulus closest to the sound source, and, it successfully oriented towards the target object based on visual attributes alone (see FIG. 7A).

The physical embodiment of the brain-based device was important for incorporating many of the challenging aspects of this object discrimination task, such as variations in the position, scale and luminosity of visual images, sound reflections, and slippages during movement. Reliance on elaborate computer simulations risks introducing a priori biases in the form of implicit instructions governing interactions between an agent and its environment. By the use of a real-world environment, however, not only is the risk of introducing such biases avoided, but also the need for the construction of a highly complex simulated environment is eliminated.

The simulated nervous system 12 of the present invention contains cortical areas analogous to the ventral occipito-temporal stream of the visual system (areas V2, V4, and IT), the motor system (area C), as well as reward or value systems (area S) analogous to diffuse ascending neuromodulatory systems. None of these specialized areas, however, nor preferential directions of information flow (e.g. "top-down" or "bottom-up"), are by themselves sufficient for binding the features of visual objects. Rather, visual binding in the brain-based device BBD is achieved through the interaction of local processes (i.e. activity in each simulated neural area), and global processes (i.e. emergent functional circuits characterized by synchronous activity distributed throughout the simulated nervous system 12). Reentrant connections among distributed neural areas V1, V2, etc. were found to be essential for the formation of these circuits (see FIGS. 9, 10, and 12) and for successful performance in a task requiring discrimination between multiple objects with shared features (see FIG. 7). The brain-based device BBD of the present invention achieved reliable discriminations in the visual field, which resulted from self-generated or autonomous movement in a rich real-world environment (see FIG. 11).

The state of each neuronal unit in the simulated nervous system 12 has been described by both a firing rate variable and a phase variable, where post-synaptic phase tends to be correlated with the phase of the most strongly active pre-synaptic inputs. This modeling strategy provided the temporal precision needed to represent neural synchrony, without incurring the computational costs associated with modeling of the spiking activity of individual neurons. While representation of precise spike timing is necessary for modeling certain neuronal interactions, the disclosed model suggests that for the purposes of illustrating the mechanism for visual binding, such detail is not required. It is also important to emphasize that phase in the described model is not intended as a reflection of possible underlying oscillatory activity, specifically, it should not be taken to imply that regular brain oscillations at specific frequencies are an essential component of the neural mechanisms of binding.

Although local regions in the simulated nervous system 12 had segregated functions based on their input and connectivity, object recognition and object discriminative behavior was an emergent property of the whole system, not of any individual area. The neural responses of the brain-based device BBD during an orienting movement toward a target showed this global property in terms of synchronized activity among a dynamic set of neuronal units in different neural areas (see FIGS. 8 and 9A). The simultaneous viewing of two objects clearly evoked two distinct sets of circuits that were distributed throughout the simulated nervous system 12 and distinguished by differences in the relative timing of their activity. When the reentrant connections between neural areas V1, V2, etc. were removed via simulated lesions, coherent interactions among these neural areas were disrupted (see FIGS. 9B, 10B, and 10C) resulting in failures in both object perceptual categorization and object discriminative behavior (see FIG. 7B).

Both experience and value shape the global properties of the simulated nervous system 12. This is clearly shown in FIGS. 12A and 12B where, during early training, area S showed no activity, and area C showed no bias toward the target object until the onset of the auditory cue, i.e. value. Late in the training, area S became active well before the auditory cue onset as a result of the value-dependent plastic connections from area IT to area S, i.e. value of visual stimuli. Activity in area S therefore became predictive of the unconditioned stimuli (i.e. the auditory tone). Value-dependent plastic connections from area IT to area C and excitatory connections from area S to area C ensured that this shift in the timing of value-related activity resulted in a bias in the activity of area C which favored movement toward the target in preference to the distracter. This emphasizes the role of value systems in modifying the efficacy of distributed neural connections to assure adaptive behavior. Successful performance in the object discrimination task amongst objects in a visual field required the complementary action of neural synchrony and experience-dependent changes in neuronal firing rates (see Table 3). Neuronal synchrony, which was indicated by groups of neuronal units sharing a similar phase, was necessary for the formation of multiple global circuits corresponding to each object in view. At the same time, the activity of the neuronal units within these circuits influenced activity levels in areas V4, IT, and C causing NOMAD 10 to favor the target object over distracters. These observations suggest that mean firing rate "codes" and synchrony-based "codes" need not be considered as mutually exclusive explanations of neuronal function.

A prediction of the described model, in which neuronal units represent the activity of small groups of neurons, is that neural synchrony at the group level, rather than zero phase lag among individual neurons, may be sufficient for sensory binding. Although some single-unit recording studies have shown that neurons activated by attended stimuli are more synchronized than neurons activated by unattended stimuli, synchronous activity among single units has been difficult to detect in tasks requiring binding. Also, micro-electrode recordings from primate prefrontal cortex have shown higher levels of correlated firing among local, inhibitory neurons than among excitatory, long-range pyramidal neurons. On the other hand, neuromagnetic recordings of human subjects during binocular rivalry have shown an increase in the intra- and inter-hemispheric coherence of signals associated with a perceptually dominant stimulus, as compared to a stimulus which is not consciously perceived. However, neuromagnetic signals do not reflect reentrant relations between single neurons; rather, they represent averages across large neuronal populations. This is therefore consistent with the model of the present invention described above in suggesting that synchrony can operate at a neuronal group level as well as at the single neuron level.

Higher brain function depends on the cooperative activity of the entire nervous system, reflecting its morphology, its dynamics, and its interactions with the body and the environment. In accord with theoretical views emphasizing the importance of binding through synchrony the brain-based device BBD of the present invention shows that visual binding and object discrimination can arise as a result of the constraints reentry and behavior impose on interactions between local processes (activity in particular neural areas) and global processes (synchronously active and broadly distributed neural circuits). This interaction between these processes was essential, and neither specialized areas nor deterministic preferential directions of information flow were sufficient alone to achieve visual binding.

The foregoing description of the preferred embodiments of the present invention has been provided for purposes of illustration and description. It is not intended to be exhaustive or to limit the invention to the precise forms disclosed. Many modifications and variations will be apparent to the practitioner skilled in the art. Embodiments were chosen and described in order to best explain the principles of the invention and its practical application, thereby enabling others skilled in the art to understand the invention, the various embodiments and with various modifications that are suited to the particular use contemplated. It is intended that the scope of the invention be defined by the following claims and their equivalents.

What is claimed is:

1. A mobile brain-based device for behaving in a real-world environment to integrate a visual scene, comprising:
   a. a mobile adaptive device having
      i. a visual input sensor for receiving visual information;
      ii. an auditory input sensor for receiving auditory information; and
      iii. an effector for enabling movement of said mobile adaptive device;
   b. a computer-based simulated nervous system corresponding to the cortical regions of a human brain for binding different visual features of an object within the visual scene, said computer-based simulated nervous system including
  i. a first neural area forming a visual system and responsive to visual input from said visual input sensor for producing visual stimuli, said first neural area corresponding to the ventral cortical pathway of the brain for producing visual stimuli, said first neural area including neural areas V1, V2, V4 and IT being coupled in a pathway V1→V2→V4→IT;
  ii. a second neural area forming an auditory system and responsive to auditory input from said auditory input sensor for producing auditory stimuli;
  iii. a third neural area, analogous to an ascending neuromodulatory system, responsive to a real-world salient event experienced by the mobile brain-based device while being mobile in its real-world environment, for producing value stimuli; and
  iv. a fourth neural area, forming a tracking system and responsive to said auditory, visual and value stimuli, for controlling said effector to orient said mobile adaptive device towards the auditory and visual input information to said mobile adaptive device, said fourth neural area corresponding to the superior colliculus area of the brain; and
c. wherein visual binding is achievable during real-world mobility of said mobile adaptive device through reentrant connectivity of neuronal units within each of said first, second, third and fourth neural areas, through reentrant connectivity between said first, second, third and fourth neural areas, and through the interaction of local processes, which are activities within each of said first, second, third and fourth neural areas, and global processes which create functional neural circuits formed during the real-world operation and having synchronous activity between said first, second, third and fourth neural areas.

2. A mobile brain-based device according to claim 1, wherein said neural area $V_1$ is divided into sub-regions having neuronal units responding to colors and line segments of a visual object.

3. A mobile brain-based device according to claim 1, wherein said neural area $V_2$ has neuronal units whose receptive fields correspond to pixels of said visual input sensor.

4. A mobile brain-based device for behaving in a real-world environment to integrate a visual scene, comprising:
a. a mobile adaptive device having
  i. a visual input sensor for receiving visual information;
  ii. an auditory input sensor for receiving auditory information; and
  iii. an effector for enabling movement of said mobile adaptive device;
b. a computer-based simulated nervous system corresponding to the cortical regions of a human brain for binding different visual features of an object within the visual scene, said computer-based simulated nervous system including
  i. a first neural area forming a visual system and responsive to visual input from said visual input sensor for producing visual stimuli, said first neural area corresponding to the ventral cortical pathway of the brain for producing visual stimuli;
  ii. a second neural area forming an auditory system and responsive to auditory input from said auditory input sensor for producing auditory stimuli;
  iii. a third neural area, analogous to an ascending neuromodulatory system, responsive to a real-world salient event experienced by the mobile brain-based device while being mobile in its real-world environment, for producing value stimuli; and
  iv. a fourth neural area, forming a tracking system and responsive to said auditory, visual and value stimuli, for controlling said effector to orient said mobile adaptive device towards the auditory and visual input information to said mobile adaptive device, said fourth neural area corresponding to the superior colliculus area of the brain;
c. wherein each neuronal unit in each said first, second, third and fourth neural area has relative neuronal activity whose timing is represented by a firing rate variable and the relative timing of which is represented by a phase variable, in which similar firing phases of neuronal units reflect synchronous activity; and
d. wherein visual binding is achievable during real-world mobility of said mobile adaptive device through reentrant connectivity of neuronal units within each of said first, second, third and fourth neural areas, through reentrant connectivity between said first, second, third and fourth neural areas, and through the interaction of local processes, which are activities within each of said first, second, third and fourth neural areas, and global processes which create functional neural circuits formed during the real-world operation and having synchronous activity between said first, second, third and fourth neural areas.

* * * * *